United States Patent
Low

(10) Patent No.: US 11,672,459 B2
(45) Date of Patent: Jun. 13, 2023

(54) LOCALIZED COLLECTION OF BIOLOGICAL SIGNALS, CURSOR CONTROL IN SPEECH-ASSISTANCE INTERFACE BASED ON BIOLOGICAL ELECTRICAL SIGNALS AND AROUSAL DETECTION BASED ON BIOLOGICAL ELECTRICAL SIGNALS

(71) Applicant: Neurovigil, Inc., La Jolla, CA (US)

(72) Inventor: Philip Low, La Jolla, CA (US)

(73) Assignee: NEUROVIGIL, INC., Moffett Field, CA (US)

( * ) Notice: Subject to any disclaimer, the term of this patent is extended or adjusted under 35 U.S.C. 154(b) by 365 days.

(21) Appl. No.: 15/028,887

(22) PCT Filed: Oct. 14, 2014

(86) PCT No.: PCT/US2014/060489
§ 371 (c)(1),
(2) Date: Apr. 12, 2016

(87) PCT Pub. No.: WO2015/057709
PCT Pub. Date: Apr. 23, 2015

(65) Prior Publication Data
US 2016/0256067 A1 Sep. 8, 2016

Related U.S. Application Data

(60) Provisional application No. 61/890,859, filed on Oct. 14, 2013.

(51) Int. Cl.
*A61B 5/00* (2006.01)
*A61B 5/05* (2021.01)
(Continued)

(52) U.S. Cl.
CPC .............. *A61B 5/296* (2021.01); *A61B 5/291* (2021.01); *A61B 5/316* (2021.01); *A61B 5/374* (2021.01);
(Continued)

(58) Field of Classification Search
CPC ... A61B 5/0478; A61B 5/0476; A61B 5/0006; A61B 5/6803; A61B 5/742;
(Continued)

(56) References Cited

U.S. PATENT DOCUMENTS

| 4,595,013 A | * | 6/1986 | Jones | ................. | A61B 5/04085 |
| | | | | | 600/383 |
| 5,047,930 A | * | 9/1991 | Martens | ................. | A61B 5/389 |
| | | | | | 706/924 |

(Continued)

FOREIGN PATENT DOCUMENTS

| WO | WO 2006/121455 A1 | 11/2006 |
| WO | WO 2009/069134 A2 | 6/2009 |

(Continued)

OTHER PUBLICATIONS

Brumberg et al. "Brain-Computer Interfaces for Speech Communication" Speech Commun. Apr. 1, 2010; 52(4): 367-379.*

(Continued)

*Primary Examiner* — Joseph A Stoklosa
*Assistant Examiner* — Brian M Antiskay
(74) *Attorney, Agent, or Firm* — Kilpatrick Townsend & Stockton LLP

(57) ABSTRACT

The present disclosure provides a device with electrodes configured to record electrical activity that are confined to a restricted area, using recorded biological electrical signals to control cursor position in a speech-assistance interface, and using recorded biological signals to detect arousals during sleep.

41 Claims, 22 Drawing Sheets

(51) Int. Cl.
  *A61B 5/296* (2021.01)
  *A61B 5/291* (2021.01)
  *A61B 5/316* (2021.01)
  *A61B 5/374* (2021.01)
  *A61B 5/389* (2021.01)

(52) U.S. Cl.
  CPC ............ *A61B 5/389* (2021.01); *A61B 5/4812* (2013.01); *A61B 5/4815* (2013.01); *A61B 5/4842* (2013.01); *A61B 5/4848* (2013.01); *A61B 5/6814* (2013.01); *A61B 5/6833* (2013.01); *A61B 5/7246* (2013.01); *A61B 5/7282* (2013.01); *A61B 5/4076* (2013.01); *A61B 5/7207* (2013.01)

(58) Field of Classification Search
  CPC ... A61B 5/6814; A61B 5/0488; A61B 5/4094; A61B 5/6833; A61B 5/01; A61B 5/746; A61B 2560/0475; A61B 5/04; A61B 5/4064; A61B 5/4088; A61B 5/4812; A61B 5/4836; A61B 5/0002; A61B 2560/0468; A61B 5/4806; A61B 5/044; A61B 5/0482; A61B 5/04842; A61B 5/4076; A61B 5/6868; A61B 5/7221; A61B 5/0042; A61B 5/4809; A61B 5/486; A61B 5/4815; A61B 5/4821; A61B 5/316; A61B 5/369; A61B 5/165; A61B 5/291; A61B 5/7203; G06F 19/00; A61N 1/0456; A61N 1/053
  USPC ....... 600/372, 382–384, 386, 388, 391, 393, 600/544–545; 607/115
  See application file for complete search history.

(56) References Cited

U.S. PATENT DOCUMENTS

| | | | | |
|---|---|---|---|---|
| 5,772,591 | A * | 6/1998 | Cram | A61B 5/4041 600/383 |
| 6,272,378 | B1 * | 8/2001 | Baumgart-Schmitt | A61B 5/0476 600/544 |
| 7,860,561 | B1 * | 12/2010 | Modarres | A61B 5/726 600/544 |
| 8,073,534 | B2 * | 12/2011 | Low | A61B 5/4815 600/544 |
| 8,606,356 | B2 | 12/2013 | Lee et al. | |
| 8,617,068 | B2 | 12/2013 | Doherty et al. | |
| 8,909,317 | B1 * | 12/2014 | Bibian | A61B 5/0478 600/383 |
| 2005/0004489 | A1 * | 1/2005 | Sarkela | A61B 5/0478 600/544 |
| 2005/0076908 | A1 | 4/2005 | Lee et al. | |
| 2005/0217674 | A1 * | 10/2005 | Burton | A61B 5/145 128/204.23 |
| 2006/0258930 | A1 * | 11/2006 | Wu | A61B 5/0002 600/383 |
| 2006/0293608 | A1 * | 12/2006 | Rothman | A61B 5/0476 600/545 |
| 2007/0060831 | A1 * | 3/2007 | Le | A61B 5/0476 600/544 |
| 2007/0225585 | A1 * | 9/2007 | Washbon | A61B 5/0478 600/393 |
| 2008/0001735 | A1 * | 1/2008 | Tran | G06F 19/3418 340/539.22 |
| 2009/0024044 | A1 * | 1/2009 | Virtanen | A61B 5/053 600/509 |
| 2009/0099473 | A1 * | 4/2009 | Dunseath | A61B 5/6814 600/544 |
| 2009/0105577 | A1 * | 4/2009 | Wu | A61B 5/0478 600/383 |
| 2009/0318826 | A1 * | 12/2009 | Green | A61B 5/4851 600/545 |
| 2010/0049008 | A1 | 2/2010 | Doherty et al. | |
| 2010/0217146 | A1 * | 8/2010 | Osvath | A61B 5/0478 600/544 |
| 2011/0098593 | A1 | 4/2011 | Low et al. | |
| 2011/0218454 | A1 | 9/2011 | Low | |
| 2011/0295096 | A1 * | 12/2011 | Bibian | A61B 5/0478 600/372 |
| 2012/0065536 | A1 * | 3/2012 | Causevic | A61B 5/0476 600/544 |
| 2013/0079618 | A1 * | 3/2013 | Sandmore | A61B 5/0478 600/393 |
| 2014/0206975 | A1 * | 7/2014 | Lang | A61B 5/04001 600/391 |

FOREIGN PATENT DOCUMENTS

| | | | |
|---|---|---|---|
| WO | WO 2010/015838 | A3 | 5/2010 |
| WO | WO 2010/057119 | A2 | 5/2010 |
| WO | WO 2010/147913 | A1 | 12/2010 |
| WO | WO 2011/056679 | A2 | 5/2011 |
| WO | WO 2012/153263 | A1 | 11/2012 |

OTHER PUBLICATIONS

Extended European Search Report dated May 26, 2017, regarding EP 14 85 4640.
Chinese Office Action dated Jun. 1, 2018, regarding CN 2014800669767.
"Notice of Acceptance", issued by the Australian Patent Office dated Jul. 6, 2021, for Application No. AU2019204112, 3 pages.
"Office Action" issued by the European Patent Office dated Aug. 9, 2021, for Application No. EP14854640.1, Office Action dated Aug. 9, 2021, 4 pages.
"First Examination Report", issued by the India Patent Office dated Jul. 16, 2021, for Application No. IN201647016563, 5 pages.
Australian Application No. 2021250913, Office Action, dated Dec. 9, 2022, 5 pages.

* cited by examiner

LOCALIZED COLLECTION OF BIOLOGICAL SIGNALS, CURSOR CONTROL IN SPEECH-ASSISTANCE INTERFACE BASED ON BIOLOGICAL ELECTRICAL SIGNALS AND AROUSAL DETECTION BASED ON BIOLOGICAL ELECTRICAL SIGNALS

CROSS REFERENCE TO RELATED APPLICATIONS

This application is a 35 USC § 371 National Stage application of International Application No. PCT/US2014/060489 filed Oct. 14, 2014, now pending; which claims the benefit under 35 USC § 119(e) to U.S. Application Serial No. 61/890,859 filed Oct. 14, 2013, now expired. The disclosure of each of the prior applications is considered part of and is incorporated by reference in the disclosure of this application.

BACKGROUND OF THE INVENTION

Field of the Invention

The present disclosure relates generally to medical devices, and more particularly to a device with electrodes configured to record electrical activity that are confined to a restricted area, using recorded biological electrical signals to control cursor position in a speech-assistance interface, and using recorded biological signals to detect arousals during sleep.

Background Information

In humans, various neurons in the brain cooperate to generate a rich and continuous set of neural electrical signals. Such signals have powerful influence on the control of the rest of our bodies. For example, the signals initiate body movements and facilitate cognitive thoughts. Further, neural signals can cause humans to wake during sleep. Despite decades of intense research, due to the complexity of the signals, a direct translation from signals to various human actions remains unknown. However, the utility of understanding such a mapping offers the potential to greatly improve the lives of many individuals who are handicapped in a life function. The understanding would presumably thereafter allow a condition to be diagnosed or a particular signal-to-action biological pathway to be circumvented and/or replicated by technology.

SUMMARY

A variety of devices have, over the years, been used to record neural activity. One such device includes an electroencephalography (EEG) device. Traditionally, dozens of electrodes are placed all around a person's head. A large number of electrodes are precisely placed on scalp locations in an effort to improve signal-to-noise ratios. Even despite the many electrodes used, many continue to assert that EEG has poor spatial resolution and a low signal-to-noise ratio. Thus, applications of EEG data are limited for at least two reasons: the number of electrodes and placement precision typically limit EEG recordings to clinical settings, and previous struggles to extract meaningful neural underpinnings in the data constrain interpretations and uses for the data.

Certain embodiments of the present invention can capitalize on discovered techniques for recognizing neural signatures within EEG data previously discarded as being too noisy for significant interpretation. For example, in some embodiments, a single, small device can house multiple EEG electrodes, including an active electrode, a reference electrode and (optionally) a ground electrode. This device can have a footprint with a length and width less than 6 (or even 4) inches, and separation distances between any pair of electrodes can be less than 3 inches. Such proximate location of the active and reference electrodes has been traditionally avoided, as it was thought to induce distortion into the recordings. Further, because EEG analysis typically differentially amplifies signals from the two electrodes, placing the reference electrode at a location where it itself will be recording neural activity has been thought to inhibit detection of neural signals of interest (typically in a high-frequency band). Thus, a reference electrode is traditionally placed far from an active electrode and at a neutral location with relatively low or no neural activity. Nevertheless, processing of data from clustered electrodes, as described herein, can nonetheless extract signals of physiological significance.

Signals recorded using the electrodes can be collectively analyzed (e.g., at the device) to generate a single channel of neural recordings. This channel can then be analyzed to, e.g., identify an absolute or relative amount of sleep time in various sleep stages, to assess a number and type of potential sleep disturbances and/or to identify sleep abnormalities.

In one instance, a spectrogram of a recorded signal is normalized one or more times across time bins and/or across frequencies. For example, in one instance, the spectrogram can be normalized once across time bins. In another instance, the spectrogram is normalized across time bins and then across frequencies. In yet another instance, an alternating pattern of time-bin and frequency normalization can continue to reach a given number of normalizations or until a normalization factor is below a threshold. Normalization across time bins can include calculating a z-score, for each frequency in a spectrogram, using all powers for that frequency in the spectrogram. The powers for that frequency can be normalized by the z-score. Normalization across frequencies can include calculating a z-score, for each time bin in the spectrogram, using all powers for that time bin in the spectrogram. The powers for that time bin can be normalized by the z-score.

In some instances, for each time bin in a normalized spectrum, a "strong frequency" for that time bin can be defined as the frequency associated with a high (e.g., above an absolute or relative threshold) or a highest normalized power for the time block. Thus, a time-series strong-frequency function can be determined. Distributions of strong frequencies can vary across sleep stages, such that identifying strong frequencies can support an estimation of an associated sleep stage.

Further, at each time point, a fragmentation value can be defined. The fragmentation value can include a temporal fragmentation value or a spectral fragmentation value. For the temporal fragmentation value, a temporal gradient of the spectrogram can be determined. The spectrogram can include a raw spectrogram and/or a spectrogram having been normalized 1, 2 or more times across time bins and/or across frequencies (e.g., a spectrogram first normalized across time bins and then across frequencies). Thus, each time bin can be associated with a vector (spanning a set of frequencies) of partial-derivative power values. For a given time block or epoch (including multiple time bins), a frequency-specific variable can be determined for each frequency using gradient values within the time block and corresponding to a given frequency. For example, the frequency-specific variable can include a mean of an absolute value of the gradient values corresponding to a given frequency. A temporal fragmentation value can then be defined as a frequency or epoch corresponding to a high or highest frequency-specific variable. Thus, the temporal fragmentation value can identify a frequency with high modulation. A spectral fragmentation value can be similarly defined but can be based on a spectral gradient of the spectrogram. High fragmentation values can be indicative of a sleep-stage disturbance or changes in waking activity.

Analysis of channel data can occur (in full or in part) at the device or at a remote device. For example, channel data (or signals giving rise to the channel data) can be (e.g., wirelessly) transmitted to other resources for more intensive processing and/or storage. It will be appreciated that the device can also collect, transmit and/or analyze non-EEG data The device can also include one or more other external sensors, such as an accelerometer to provide additional data indicative of a context of a recording (e.g., to allow for differentiate between a stationary and active state) or a thermometer to estimate a temperature of a user.

The device can be positioned on a person using by adhering an adhesive material to the device and to a person. For example, an adhesive material (e.g., a double-sided adhesive film or substance) can be applied to at least part of an under side of a device, such that it can attach the device to a skin location. As another example, an adhesive film can be positioned over the device, and a portion of the film extending beyond the device can attach to a skin location.

Thus, the device and techniques as described herein allow for EEG to be easily collected. A single device can independently provide data for a complete channel, and both the number of required scalp applications and the requisite placement can be is relatively low. Thus, a patient can himself apply the device and initiate EEG recordings. The wireless transmission from the device further reduces the complication of commencing data collection. It will be appreciated that, while a multi-electrode device can independently support a channel, multiple devices (in some instances) can be used to further enrich the recording by collecting multiple channels.

Embodiments herein can extend beyond the collection, analysis and application of neural signals: the device can be used to collect any biological electrical signal. For example, the device can be positioned over a muscle and can collect electromyography (EMG) data. The EMG data can be used, e.g., for biofeedback training (e.g., by providing a cue to a patient indicative of when a muscle is being activated), to aid in diagnosis of a neuropathic or myopathic disease and/or to translate a muscle movement into control of an external object (e.g., a cursor on a screen of an electronic device or control of a prosthetic). In an exemplary embodiment, one or more devices can be used to allow sufferers of amyotrophic lateral sclerosis (ALS) to communicate despite restricted vocalization and hand-control capabilities. Specifically, one or more devices can be positioned on a single or multiple muscles which the patient can still control, such as a jaw muscle. Simultaneously, the patient can be presented with a screen with multiple text options, such as individual letters, letter combinations, words or phrases. Analysis of recordings from the jaw muscle can cause the cursor to move to a desired text option. Repetition of such selections can allow sentences to be formed, which can be used for written communications or can be spoken by an automated reader.

EMG recordings may be mapped to cursor movements. In one instance, this mapping can be determined based on, e.g., analyzing raw EMG data from one or more channels (for training or non-training situations) using a clustering and/or component analysis to determine which signal signatures are to be associated with particular cursor movements. In one instance, particular strong frequencies are associated with cursor movements, such that (for example) muscle data dominated with strong frequencies in a high-frequency band can be determined to correspond to an upward cursor movement. In another instance, particular fragmentation values can be associated cursor movements. For example, high fragmentation values associated with one muscle's EMG can be associated with a first cursor movement, and high fragmentation values associated with another muscle's EMG can be associated with a second cursor movement.

The sensitivity and non-intrusiveness of the device and techniques can also be used to assess physiological events that can be difficult for a patient or medical professional to otherwise detect. For example, the device can record signals during sleep, and arousals (e.g., which can include micro-arousals) can be detected. In the binary case, a basic arousal can be defined as a transition from a sleep state to an awake state. However, such a binary characterization of these states unduly simplifies the complexity of sleep. Sleep is characterized using sleep stages: stages 1-4 and a rapid-eye-movement (REM) stage. How and when a person transitions between sleep stages remains poorly understood, though time spent in various sleep stages can have physiological consequences. For example, insufficient REM sleep can impair learning abilities, and stage-4 sleep is important to growth and development.

Thus, if a patient reports a poor night sleep or other sleep-related symptoms, it can be useful to monitor the stages of the patient's sleep. According to some embodiments, neural recordings can be recorded from a compact electrode device and analyzed to extract amplify high-frequency neural signals. The signals can then be categorized into sleep (or awake) stages within individual short time windows. Arousals can then be detected by quantifying the variability and/or stage transitions present within a series of time windows. The ability to categorize sleep within such short time windows enables detection of arousals that would otherwise be unrecognized. Such arousals can be used to assess a sleep quality.

This sleep analysis can further be used to detect whether a person experiences a potentially life-threatening event in their sleep. For example, tracheostomy mechanical ventilation can be performed to aid respiratory function in select patient groups (e.g., ALS, cancer of face-trauma patients) thought to benefit from the procedure. This procedure can include an insertion of a tracheostomy tube into an incision in the neck. Unfortunately, the tube has the potential to slip out of the tracheostomy. This possibility can be particularly terrifying for patients with impaired communication skills. Should their tube slip during the night, they may have difficulty alerting anyone of the problem. The device and methods disclosed herein, however, can monitor these patients' sleep stages and detect abnormal and/or concerning sleep-stage patterns. The size of the device can encourage use and monitoring compliance, and the analysis can promote detection of rapid sleep-stage patterns.

The following detailed description together with the accompanying drawings will provide a better understanding of the nature and advantages of the present invention.

DETAILED DESCRIPTION

Certain embodiments of the present invention can facilitate convenient recording of biological signals (e.g., electroencephalography (EEG) or electromyography (EMG) data) using a compact multi-electrode device. A spectrogram can be generated based on a differential of the recorded signals and normalized in one or both directions of the spectrogram (e.g., such that each power value is normalized based on power values of the same frequency but for different time bins and/or based on power values of the same time bin but for different frequencies). A spectrogram can be divided into time blocks or epochs (e.g., of a defined duration, such as 30 seconds), and each spectrogram portion can be normalized one or more times (e.g., across frequencies or across time bins in the time block). For a given time block, a z-score can be determined using the normalized power values (e.g., such that the z-score is high for frequencies corresponding to a large spread of normalized power values across time bins in the time block). A strong frequency can then be identified for the time block as being a frequency that corresponds to a high or highest normalized power. The strong frequency can be indicative of a sleep stage.

Further, for each time bin, a fragmentation value can be defined. For example, a gradient (e.g., a temporal gradient) of a (unnormalized, normalized, twice-normalized, etc.) spectrogram can be determined. For a given time block, a fragmentation value can be defined to identify a frequency corresponding to high modulation across associated powers. For example, a fragmentation value can include a frequency for which a mean of the absolute values of the gradient values (across time bins in the time block) is absolutely or relatively high. When the device records neural data during sleeping, high fragmentation values can be indicative of inconsistent sleep characteristics, which can be suggestive of sleep disturbances and/or arousals.

This technique can be effectively applied to data with short temporal binning Thus, it can recognize even very short arousals. Arousals can be indicative of poor sleep quality and/or concerning health factors. Thus, the techniques have the potential to detect potentially concerning data that otherwise may have been ignored due to larger temporal binning or an inability to collect a substantial quantity of data.

The multi-electrode device can further be used to collect EMG data from one or more muscles. Clustering and/or component techniques can be used to map features of the data with particular object actions. Thus, for example, a contraction of one muscle can indicate that a cursor is to move up, and a contraction of another muscle can indicate that a cursor is to move down. Patients with limited vocalization capabilities can then be simultaneously presented with a screen that allows them to move the cursor in directions select amongst letters, words, phrases or requests to convey a thought.

Figure 1:
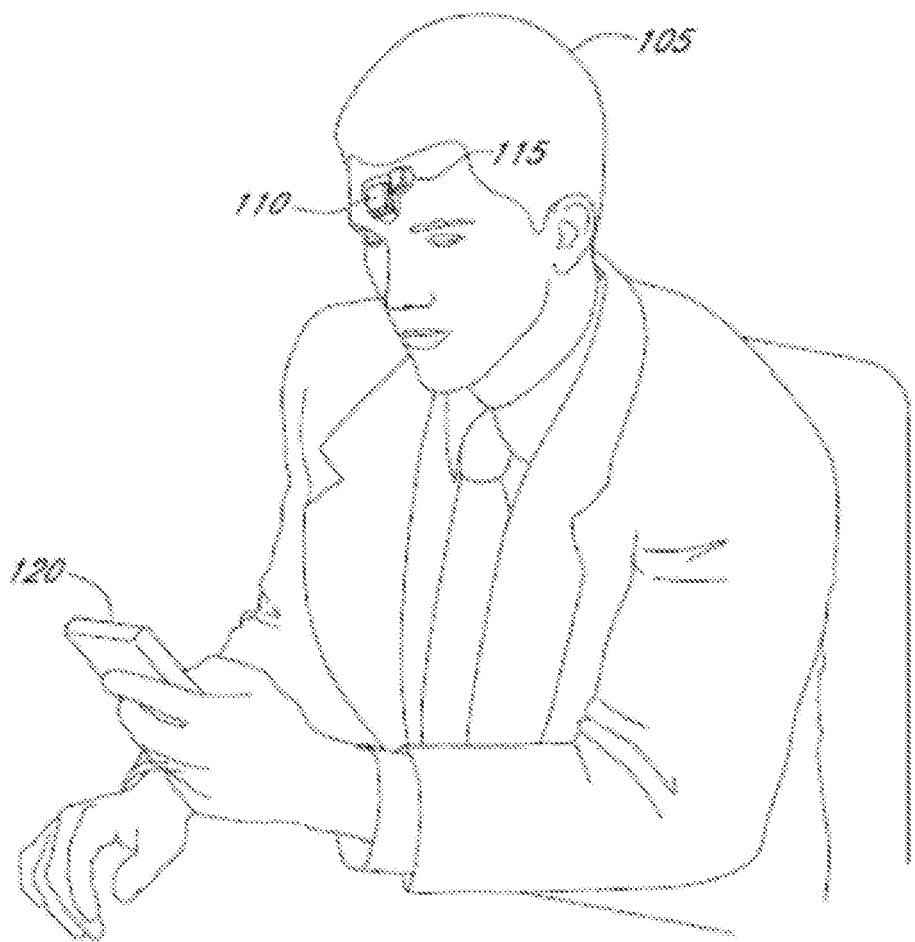
FIG. 1 shows a user wearing a multi-electrode compact device that is wirelessly communicating with another electronic device.

FIG. 1 shows a user 105 using a multi-electrode device 110. The device is shown as being adhered to the user's forehead 115 (e.g., via an adhesive positioned between the device and the user). The device can include multiple electrodes to detect and record neural signals. Subsequent to the signal recording, the device can transmit (e.g., wirelessly transmit) the data (or a processed version thereof) to another electronic device 120, such as a smart phone. The other electronic device 120 can then further process and/or respond to the data, as further described herein. Thus, FIG. 1 exemplifies that multi-electrode device 105 can be small and simple to position. While only one device is shown in this example, it will be appreciated that—in some embodiments—multiple devices are used.

Further, while FIG. 1 illustrates that an adhesive attaches device 110 to user 105, other attachment means can be used. For example, a head harness or band can be positioned around a user and the device. Also, while housing all electrodes for a channel in a single compact unit is often advantageous for ease of use, it will be appreciated that, in other instances, electrodes can be external to a primary device housing and can be positioned far from each other. In one instance, a device as descried in PCT application PCT/US2010/054346 is used. PCT/US2010/054346 is hereby incorporated by reference for all purposes.

Devices 115a and 115b can communicate directly (e.g., over a Bluetooth connection or BTLE connection) or indirectly. For example, each device can communicate (e.g., over a Bluetooth connection or BTLE connection) with a server 120, which can be located near tennis court 110.

Figure 2:
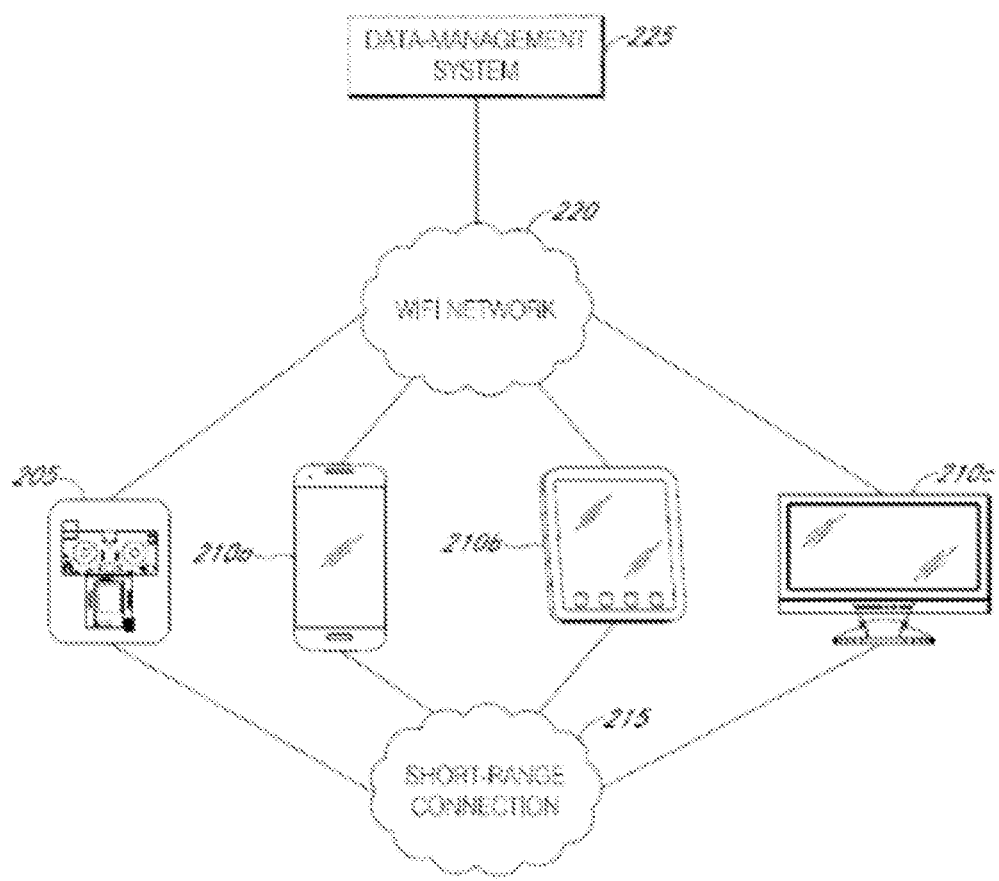
FIG. 2 shows examples of devices connected on a network to facilitate coordinated assessment and use of biological electrical recordings according to an embodiment of the present invention.

FIG. 2 shows examples of devices connected on a network to facilitate coordinated assessment and use of biological electrical recordings. One or more multi-electrode devices 205 can collect channel data derived from recorded biological data from a user. The data can then be presented to one or more other electronic devices, such as a mobile device 210a (e.g., a smart phone), a tablet 210b or laptop or a desktop computer 201c. The inter-device communication can be over a connection, such as a short-range connection 215 (e.g., a Bluetooth, BTLE or ultra-wideband connection) or over a WiFi network 220, such as the Internet.

One or more devices 205 and/or 210 can further access a data-management system 225, which can (for example) receive and assess data from a collection of multi-electrode devices. For example, a health-care provider or pharmaceutical company (e.g., conducting a clinical trial) can use data from multi-electrode devices to measure health of patients. Thus, e.g., data-management system 225 can store data in association with particular users and/or can generate population statistics.

Figure 3:
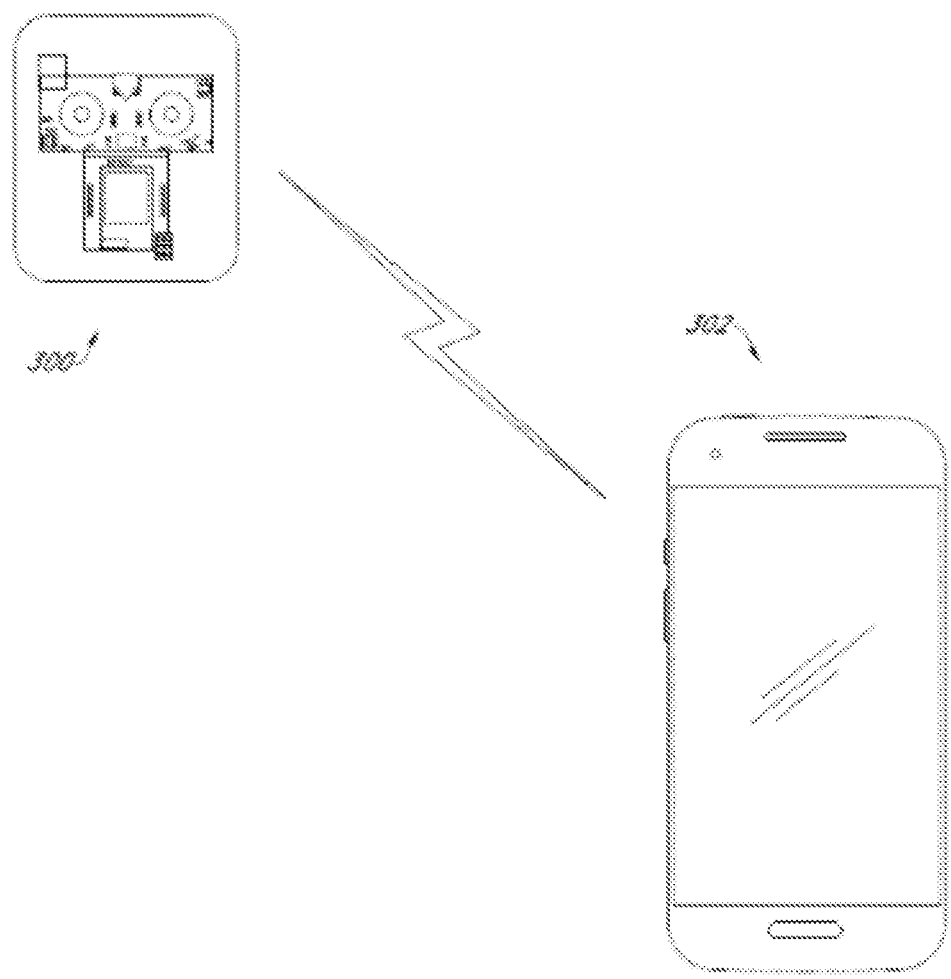
FIG. 3 shows a multi-electrode device communicating wirelessly with another electronic device according to an embodiment of the present invention.

FIG. 3 shows a multi-electrode device 300 communicating (e.g., wirelessly or via a cable) with another electronic device 302. This communication can be performed to enhance a functionality of a multi-electrode device by drawing on resources of the other electronic device (e.g., faster processing speed, larger memory, display screen, input-receiving capabilities). In one instance, electronic device 302 includes interface capabilities that allow for a user (e.g., who may, or may not be, the same person from whom signals are being recorded) to view information (e.g., summaries of recorded data and/or operation options) and/or control operations (e.g., controlling a function of multi-electrode device 300 or controlling another operation, such as speech construction). The communication between devices 300 and 302 can occur intermittently as device 300 collects and/or processes data or subsequent to a data-collection period. The data can be pushed from device 300 to other device 302 and/or pulled from other device 302.

Figure 4:
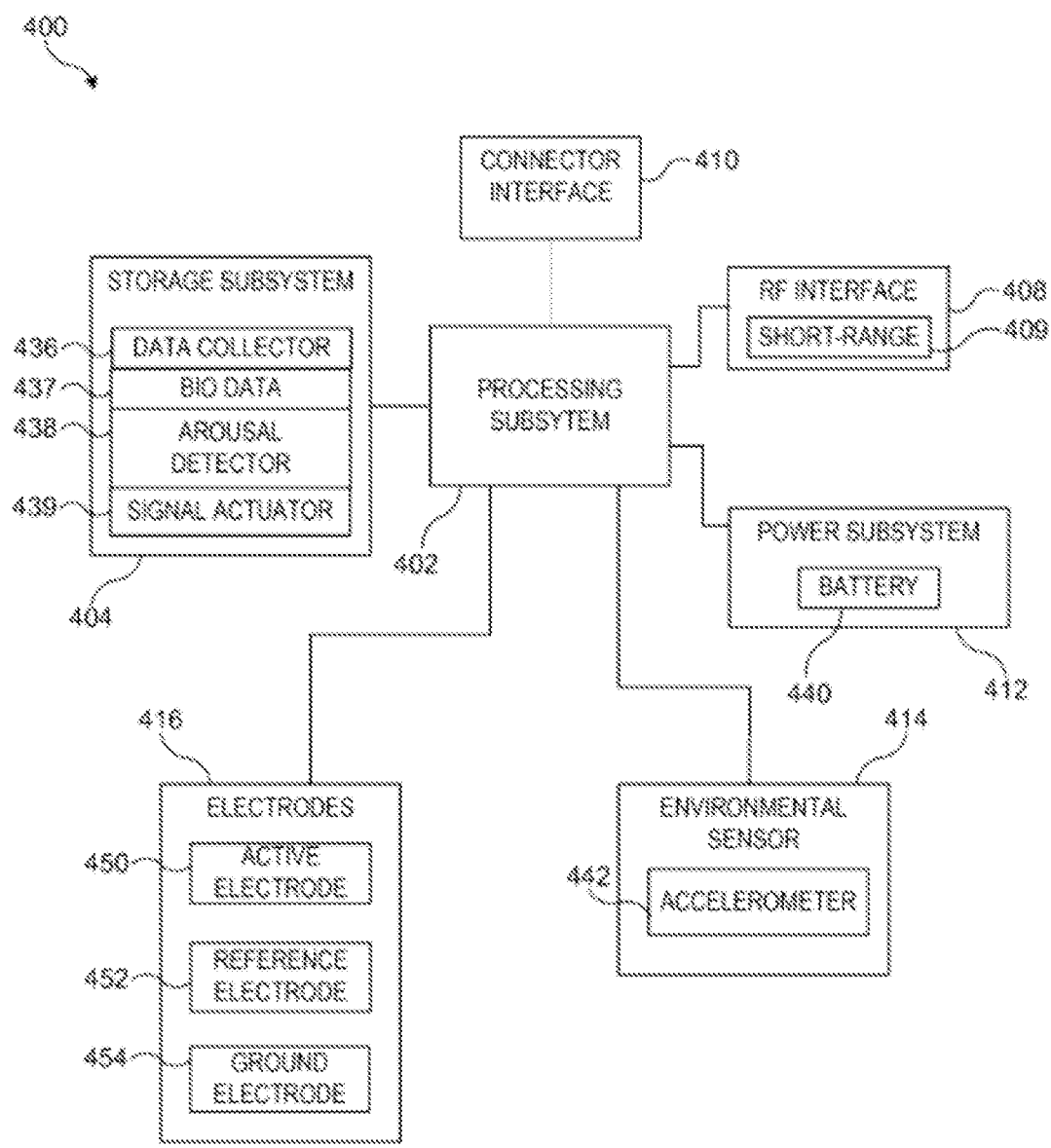
FIG. 4 is a simplified block diagram of a multi-electrode device according to an embodiment of the present invention.

FIG. 4 is a simplified block diagram of a multi-electrode device 400 (e.g., implementing multi-electrode device 300) according to an embodiment of the present invention, multi-electrode device 400 can include processing subsystem 402, storage subsystem 404, RF interface 408, connector interface 410, power subsystem 412, environmental sensors 414, and electrodes 416. Multi-electrode device 400 need not include each shown component and/or can also include other components (not explicitly shown).

Storage subsystem 404 can be implemented, e.g., using magnetic storage media, flash memory, other semiconductor memory (e.g., DRAM, SRAM), or any other non-transitory storage medium, or a combination of media, and can include volatile and/or non-volatile media. In some embodiments, storage subsystem 404 can store biological data, information (e.g., identifying information and/or medical-history information) about a user and/or analysis variables (e.g., previously determined strong frequencies or frequencies for differentiating between signal groups). In some embodiments, storage subsystem 404 can also store one or more application programs (or apps) 434 to be executed by processing subsystem 410 (e.g., to initiate and/or control data collection, data analysis and/or transmissions).

Processing subsystem 402 can be implemented as one or more integrated circuits, e.g., one or more single-core or multi-core microprocessors or microcontrollers, examples of which are known in the art. In operation, processing system 402 can control the operation of multi-electrode device 400. In various embodiments, processing subsystem 404 can execute a variety of programs in response to program code and can maintain multiple concurrently executing programs or processes. At any given time, some or all of the program code to be executed can be resident in processing subsystem 404 and/or in storage media such as storage subsystem 404.

Through suitable programming, processing subsystem 402 can provide various functionality for multi-electrode device 400. For example, in some embodiments, processing subsystem 402 can execute code that can control the collection, analysis, application and/or transmission of biological data. In some embodiments, some or all of this code can interact with an interface device (e.g., other device 302 in FIG. 3), e.g., by generating messages to be sent to the interface device and/or by receiving and interpreting messages from the interface device. In some embodiments, some or all of the code can operate locally to multi-electrode device 400.

Processing subsystem 402 can also execute a data collection code 436, which can cause data detected by electrodes 416 to be recorded and saved. In some instances, signals are differentially amplified and filtering can be applied. The signals can be stored in a biological-data data store 437, along with recording details (e.g., a recording time and/or a user identifier). The data can be further analyzed to detect physiological correspondences. As one example, processing of a spectrogram of the recorded signals can reveal frequency properties that correspond to particular sleep stages. As another example, an arousal detection code 438 can analyze a gradient of the spectrogram to identify and assess sleep-disturbance indicators and detect arousals. As yet another example, a signal actuator code 439 can translate particular biological-signal features into a motion of an external object (e.g., a cursor). Such techniques and codes are further described herein.

RF (radio frequency) interface 408 can allow multi-electrode device 400 to communicate wirelessly with various interface devices. RF interface 408 can include RF transceiver components such as an antenna and supporting circuitry to enable data communication over a wireless medium, e.g., using Wi-Fi (IEEE 802.11 family standards), Bluetooth® (a family of standards promulgated by Bluetooth SIG, Inc.), or other protocols for wireless data communication. In some embodiments, RF interface 408 can implement a short-range sensor (e.g., Bluetooth, BLTE or ultra-wide band) proximity sensor 409 that supports proximity detection through an estimation of signal strength and/or other protocols for determining proximity to another electronic device. In some embodiments, RF interface 408 can provide near-field communication ("NFC") capability, e.g., implementing the ISO/IEC 18092 standards or the like; NFC can support wireless data exchange between devices over a very short range (e.g., 20 centimeters or less). RF interface 408 can be implemented using a combination of hardware (e.g., driver circuits, antennas, modulators/demodulators, encoders/decoders, and other analog and/or digital signal processing circuits) and software components.

Multiple different wireless communication protocols and associated hardware can be incorporated into RF interface 408.

Connector interface 410 can allow multi-electrode device 400 to communicate with various interface devices via a wired communication path, e.g., using Universal Serial Bus (USB), universal asynchronous receiver/transmitter (UART), or other protocols for wired data communication. In some embodiments, connector interface 410 can provide a power port, allowing multi-electrode device 400 to receive power, e.g., to charge an internal battery. For example, connector interface 410 can include a connector such as a mini-USB connector or a custom connector, as well as supporting circuitry. In some embodiments, the connector can be a custom connector that provides dedicated power and ground contacts, as well as digital data contacts that can be used to implement different communication technologies in parallel; for instance, two pins can be assigned as USB data pins (D+ and D−) and two other pins can be assigned as serial transmit/receive pins (e.g., implementing a UART interface). The assignment of pins to particular communication technologies can be hardwired or negotiated while the connection is being established. In some embodiments, the connector can also provide connections to transmit and/or receive biological electrical signals, which can be transmitted to or from another device (e.g., device 302 or another multi-electrode device) in analog and/or digital formats.

Environmental sensors 414 can include various electronic, mechanical, electromechanical, optical, or other devices that provide information related to external conditions around multi-electrode device 400. Sensors 414 in some embodiments can provide digital signals to processing subsystem 402, e.g., on a streaming basis or in response to polling by processing subsystem 402 as desired. Any type and combination of environmental sensors can be used; shown by way of example is an accelerometer 442. Acceleration sensed by accelerometer 442 can be used to estimate whether a user is or is trying to sleep and/or estimate an activity state.

Electrodes 416 can include, e.g., round surface electrodes and can include gold, tin, silver, and/or silver/silver-chloride. Electrodes 416 can have a diameter greater than ⅛" and less than 1". Electrodes 416 can include an active electrode 450, a reference electrode 452 and (optionally) ground electrode 454. The electrodes may or may not be distinguishable from each other. The electrodes location can be fixed within a device and/or movable (e.g., tethered to a device).

Power subsystem 412 can provide power and power management capabilities for multi-electrode device 400. For example, power subsystem 414 can include a battery 440 (e.g., a rechargeable battery) and associated circuitry to distribute power from battery 440 to other components of multi-electrode device 400 that require electrical power. In some embodiments, power subsystem 412 can also include circuitry operable to charge battery 440, e.g., when connector interface 410 is connected to a power source. In some embodiments, power subsystem 412 can include a "wireless" charger, such as an inductive charger, to charge battery 440 without relying on connector interface 410. In some embodiments, power subsystem 412 can also include other power sources, such as a solar cell, in addition to or instead of battery 440.

It will be appreciated that multi-electrode device 400 is illustrative and that variations and modifications are possible. For example, multi-electrode device 400 can include a user interface to enable a user to directly interact with the device. As another example, multi-electrode device can have an attachment indicator that indicates (e.g., via a light color or sound) whether a contact between a device and a user's skin is adequate and/or whether recorded signals are of an acceptable quality.

Further, while the multi-electrode device is described with reference to particular blocks, it is to be understood that these blocks are defined for convenience of description and are not intended to imply a particular physical arrangement of component parts. Further, the blocks need not correspond to physically distinct components. Blocks can be configured to perform various operations, e.g., by programming a processor or providing appropriate control circuitry, and various blocks might or might not be reconfigurable depending on how the initial configuration is obtained. Embodiments of the present invention can be realized in a variety of apparatus including electronic devices implemented using any combination of circuitry and software. It is also not required that every block in FIG. 4 be implemented in a given embodiment of a multi-electrode device.

Figure 5:
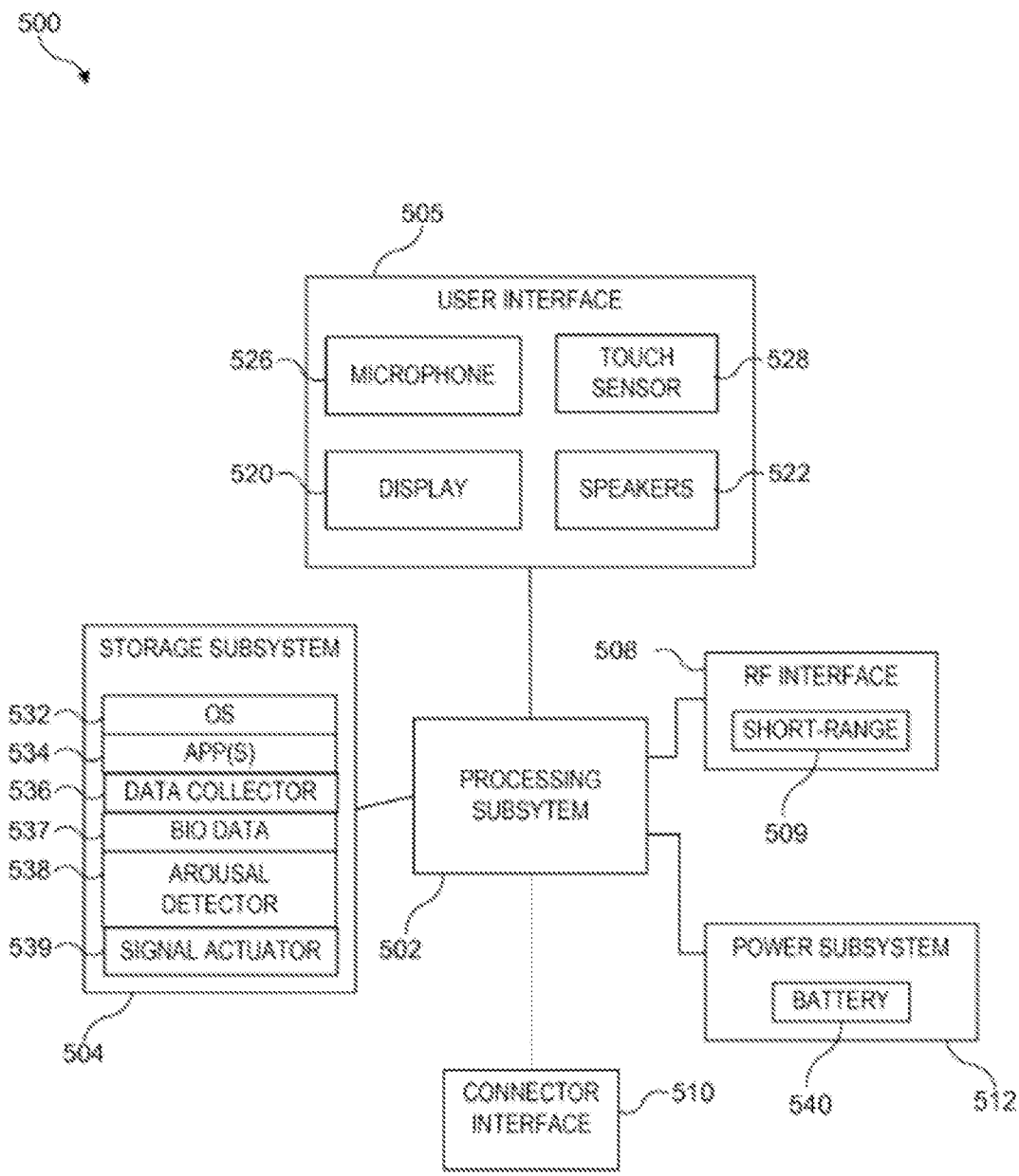
FIG. 5 is a simplified block diagram of an electronic device in communication with a multi-electrode device according to an embodiment of the present invention.

An interface device such as device 302 of FIG. 3 can be implemented as an electronic device using blocks similar to those described above (e.g., processors, storage media, RF interface, etc.) and/or other blocks or components. FIG. 5 is a simplified block diagram of an interface device 500 (e.g., implementing device 302 of FIG. 3) according to an embodiment of the present invention. Interface device 500 can include processing subsystem 502, storage subsystem 504, user interface 506, RF interface 508, connector interface 510 and power subsystem 512. Interface device 500 can also include other components (not explicitly shown). Many of the components of interface device 500 can be similar or identical to those of multi-electrode device 300 of FIG. 3.

For instance, storage subsystem 504 can be generally similar to storage subsystem 404 and can include, e.g., using magnetic storage media, flash memory, other semiconductor memory (e.g., DRAM, SRAM), or any other non-transitory storage medium, or a combination of media, and can include volatile and/or non-volatile media. Like storage subsystem 504, storage subsystem 504 can be used to store data and/or program code to be executed by processing subsystem 502.

User interface 506 can include any combination of input and output devices. A user can operate input devices of user interface 506 to invoke the functionality of interface device 500 and can view, hear, and/or otherwise experience output from interface device 500 via output devices of user interface 506. Examples of output devices include display 520 and speakers 522. Examples of input devices include microphone 526 and touch sensor 528.

Display 520 can be implemented using compact display technologies, e.g., LCD (liquid crystal display), LED (light-emitting diode), OLED (organic light-emitting diode), or the like. In some embodiments, display 520 can incorporate a flexible display element or curved-glass display element, allowing interface device 500 to conform to a desired shape. One or more speakers 522 can be provided using small-form5factor speaker technologies, including any technology capable of converting electronic signals into audible sound waves. Speakers 522 can be used to produce tones (e.g., beeping or ringing) and/or speech.

Examples of input devices include microphone 526 and touch sensor 528. Microphone 526 can include any device that converts sound waves into electronic signals. In some embodiments, microphone 526 can be sufficiently sensitive to provide a representation of specific words spoken by a user; in other embodiments, microphone 426 can be usable to provide indications of general ambient sound levels without necessarily providing a high-quality electronic representation of specific sounds.

Touch sensor 528 can include, e.g., a capacitive sensor array with the ability to localize contacts to a particular point or region on the surface of the sensor and in some instances, the ability to distinguish multiple simultaneous contacts. In some embodiments, touch sensor 428 can be overlaid over display 520 to provide a touchscreen interface, and processing subsystem 504 can translate touch events into specific user inputs depending on what is currently displayed on display 520.

Processing subsystem 502 can be implemented as one or more integrated circuits, e.g., one or more single-core or multi-core microprocessors or microcontrollers, examples of which are known in the art. In operation, processing system 502 can control the operation of interface device 500. In various embodiments, processing subsystem 502 can execute a variety of programs in response to program code and can maintain multiple concurrently executing programs or processes. At any given time, some or all of the program code to be executed can be resident in processing subsystem 502 and/or in storage media such as storage subsystem 504.

Through suitable programming, processing subsystem 502 can provide various functionality for interface device 500. For example, in some embodiments, processing subsystem 502 can execute an operating system (OS) 532 and various applications 534. In some embodiments, some or all of these application programs can interact with a multi-electrode device, e.g., by generating messages to be sent to the multi-electrode device and/or by receiving and interpreting messages from the multi-electrode device. In some embodiments, some or all of the application programs can operate locally at interface device 500.

Processing subsystem 502 can also execute a data-collection code 536 (which can be part of OS 532, part of an app or separate as desired). Data-collection code 536 can be, at least in part, complementary to data-collection code 436 in FIG. 4. In some instances, data-collection code 536 is configured such that execution of the code causes device 500 to receive raw or processed biological electrical signals (e.g., EEG or EMG signals) from a multi-electrode device (e.g., multi-electrode device 300 of FIG. 3). Data-collection code 536 can further define processing to perform on the received data (e.g., to apply filters, generate metadata indicative of a source multi-electrode device or receipt time, and/or compress the data). Data-collection code 536 can further, upon execution, cause the raw or processed biological electrical signals to be stored in a biological data store 537.

In some instances, execution of data-collection code 536 further causes device 500 to collect data, which can include biological data (e.g., a patient's temperature or pulse) or external data (e.g., a light level or geographical location). This information can be stored with biological electrical data (e.g., such that metadata for an EEG or EMG recording includes a patient's temperature and/or location) and/or can be stored separately (e.g., with a timestamp to enable future time-synched data matching). It will be appreciated that, in these instances, interface device 500 can either include the appropriate sensors to collect this additional data (e.g., a camera, thermometer, GPS receiver) or can be in communication (e.g., via RF interface 508) with another device with such sensors.

Processing subsystem 502 can also execute one or more codes that can, in real-time or retrospectively, analyze raw or processed biological electrical signals to detect events of interest. For example, execution of an arousal-detection code 538 can assess changes with a spectrogram (built using EEG data) corresponding to a sleep period of a patient to determine whether and/or when arousals occurred. In one instance, this assessment can include determining, for each time increment, a change variable corresponding to an amount by which power (e.g., normalized power) at one or more frequencies for the time increment changed relative to one or more other time increments. In one instance, this assessment can include assigning each time increment to a sleep stage and detecting time points at which the assignments changed. Sleep-staging categorizations can (in some instances) further detail any arousals that are occurring (e.g., by indicating in which stages arousals occur and/or by identifying through how many sleep stages an arousal traversed).

As another example, execution of a signal actuator code 539 can assess and translate EMG data. Initially, a mapping can be constructed to associate particular EMG signatures with particular actions. The actions can be external actions, such as actions of a cursor on a screen. The mapping can be performed using a clustering and/or component analysis and can utilize raw or processed signals recorded from one or more active electrodes (e.g., from one or more multi-electrode devices, each positioned on a different muscle).

In one instance, execution of signal actuator code 539 causes an interactive visualization to be presented on display 520. A cursor position on the screen can be controlled based on a real-time analysis of EMG data using the mapping. A person from whom the recordings are collected from can thus interact with the interface without using his hands. In an exemplary instance, the visualization can include a speech-assistance visualization that allows a person to select letters, series of letters, words or phrases. A sequential selection can allow the person to construct sentences, paragraphs or conversations. The text can be used electronically (e.g., to generate an email or letter) or can be verbalized (e.g., using a speech component of signal actuator 539 to send audio output to speakers 522) to communicate with others nearby.

RF (radio frequency) interface 508 and/or connector interface 510 can allow interface device 500 to communicate wirelessly with various other devices (e.g., multi-electrode device 400 of FIG. 4) and networks. RF interface 508 can correspond to (e.g., include a described characteristic of) RF interface 408 from FIG. 4 and/or connector interface 510 can correspond to (e.g., include a described characteristic of) connector interface 410. Power subsystem 512 can provide power and power management capabilities for interface device 512. Power subsystem 512 can correspond to (e.g., include a described characteristic of) power subsystem 41.

It will be appreciated that interface device 500 is illustrative and that variations and modifications are possible. In various embodiments, other controls or components can be provided in addition to or instead of those described above. Any device capable of interacting with another device (e.g., multi-electrode device) to store, process and/or use recorded biological electrical signals can be an interface device.

Further, while the interface device is described with reference to particular blocks, it is to be understood that these blocks are defined for convenience of description and are not intended to imply a particular physical arrangement of component parts. Further, the blocks need not correspond to physically distinct components. Blocks can be configured to perform various operations, e.g., by programming a processor or providing appropriate control circuitry, and various blocks might or might not be reconfigurable depending on how the initial configuration is obtained. Embodiments of the present invention can be realized in a variety of apparatus including electronic devices implemented using any combination of circuitry and software. It is also not required that every block in FIG. 5 be implemented in a given embodiment of a mobile device.

Communication between one or more multi-electrode devices, one or more mobile devices and an interface device can be implemented according to any communication protocol (or combination of protocols) that both devices are programmed or otherwise configured to use. In some instances, standard protocols such as Bluetooth protocols or ultra-wideband protocols can be used. In some instances, a custom message format and syntax (including, e.g., a set of rules for interpreting particular bytes or sequences of bytes in a digital data transmission) can be defined, and messages can be transmitted using standard serial protocols such as a virtual serial port defined in certain Bluetooth standards. Embodiments of the invention are not limited to particular protocols, and those skilled in the art with access to the present teachings will recognize that numerous protocols can be used.

In accordance with certain embodiments of the present invention, one or more multi-electrode devices can be conveniently used to collect electrical biological data from a patient. The data can be processed to identify signals of physiological significance. The detection itself can be useful, as it can inform a user or a third party about a patient's health and/or efficacy of a current treatment. In some instances, the signals can be used to automatically control another object, such as a computer cursor. Such a capability can extend a user's physical capabilities (e.g., which may be handicapped due to a disease) and/or improve ease of operation.

Figure 6:
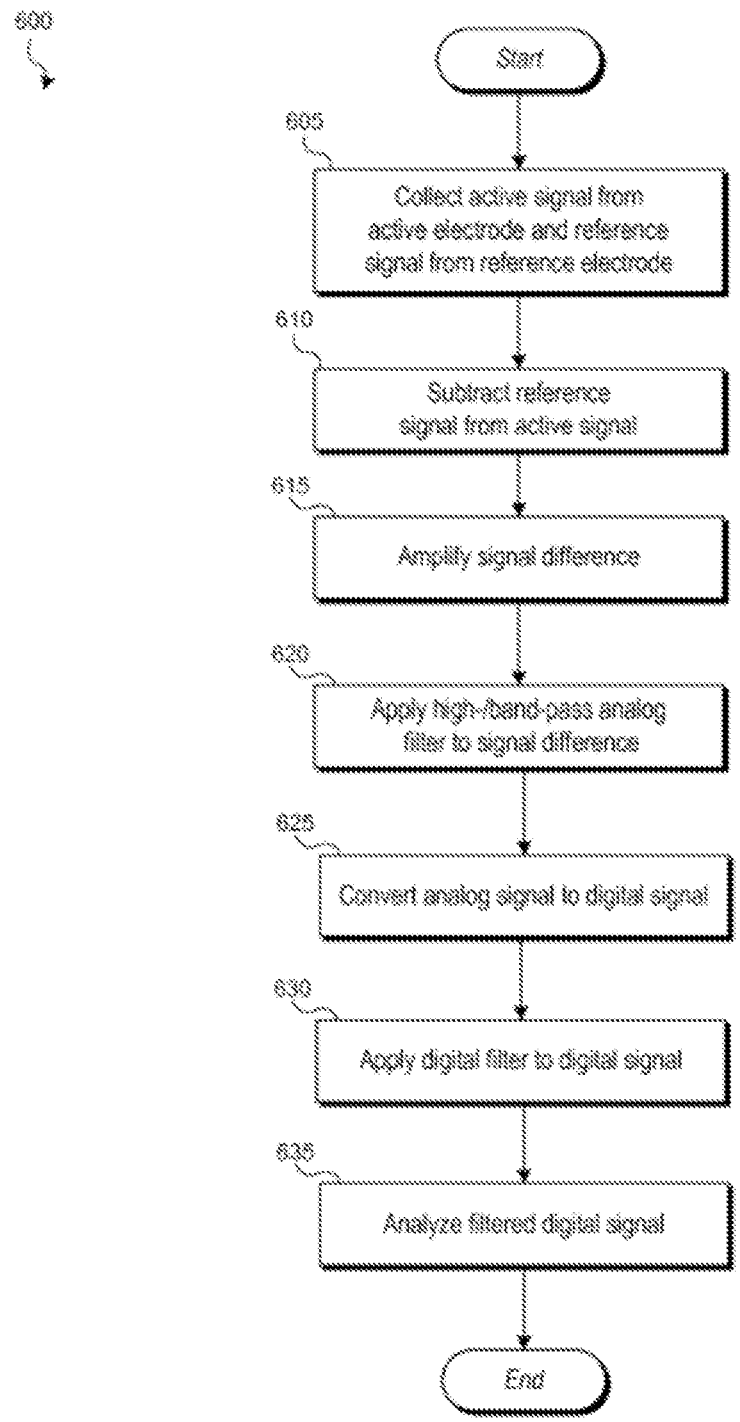
FIG. 6 is a flow diagram of a process for using a multi-electrode device to collect a channel of biological electrode data according to an embodiment of the present invention.

FIG. 6 is a flow diagram of a process 600 for using a multi-electrode device to collect a channel of biological electrode data according to an embodiment of the present invention. Part of all of process 600 can be implemented in a multi-electrode device (e.g., multi-electrode device 400). In some instances, part of process 600 (e.g., one or more of blocks 610-635) can be implemented in an electronic device that is remote from a multi-electrode device, where the blocks can be performed immediately after receiving signals from a multi-electrode device (e.g., immediately after collection), prior to storing data pertaining to a recording, in response to a request relying on collected data and/or prior to using the collected data.

At block 605, an active signal and a reference signal can be collected using respective electrodes. In some instances, a ground signal is further collected from a ground electrode. The active electrode and the reference electrode and/or the active electrode and the ground electrode can be attached to a single device (e.g., a multi-electrode device), a fixed distance from each other and/or are close to each other (e.g., such that centers of the electrodes are located less than 12, 6 or 4 inches from each other and/or such that the electrodes are positioned to likely record signals from a same muscle or same brain region).

In some instances, the reference electrode is positioned near the active electrode, such that both electrodes will likely sense electrical activity from a same brain region or from a same muscle. In other instances, the reference electrode is positioned further from the active electrode (e.g., at an area that is relatively electrically neutral, which may include an area not over the brain or a prominent muscle) to reduce overlap of a signal of interest.

Prior to the collection, the electrodes can be attached to a skin of a person. This can include, e.g., attaching a single device completely housing one or more electrodes and/or attaching one or more individual electrodes (e.g., flexibly extending beyond between a device housing). In one instances, such attachment is performed by using an adhesive (e.g., applying an adhesive substance to at least part of an underside of a device, applying an adhesive patch over and around the device and/or applying an double-sided adhesive patch under at least part of the device) to attach a multi-electrode device including the active and reference electrodes to a person. For an EEG recording, the device can be attached, e.g., near the person's frontal lobe (e.g., on her forehead). For an EMG recording, the device can be attached over a muscle (e.g., over a jaw muscle or neck muscle).

In some instances, only one active signal is recorded at a time. In other instances, each of a set of active electrodes records an active signal. In this situation, the active electrodes can be positioned at different body locations (e.g., on different sides of the body, on different muscle types or on different brain regions). Each active electrode can be associated with a reference electrode or fewer references may be collected relatively to a collected number of active signals. Each active electrode can be present in a separate multi-electrode device.

At block 610, the reference signal can be subtracted from the active electrode. This can reduce noise in the active signal, such as recording noise or noise due to a patient's breathing or movement. Though proximate location of the reference and active electrodes has been traditionally shunned, such locations can improve the portion of the active electrode's noise (e.g., patient movement noise) that will be shared at the reference electrode noise. For example, if a patient is rolling over, a movement that will be experienced by an active electrode positioned over brain center F7 will be quite different from movement experienced by a reference electrode positioned on a contralateral ear. Meanwhile, if both electrodes are positioned over a same F7 region, they will likely experience similar movement artifacts. While the signal difference may lose representation of some cellular electrical activity from an underlying physiological structure, a larger portion of the remaining signal can be attributed to such activity of interest (due to the removal of noise).

At block 615, the signal difference can be amplified. An amplification gain be, e.g., between 100 and 100,000. At block 620, the amplified signal difference can be filtered. The applied filter can include, e.g., an analog high-pass or band-pass filter. The filtering can reduce signal contributions from flowing potentials, such as breathing. The filter can include a lower cut-off frequency around 0.1-1 Hz. In some instances, the filter can also include a high cut-off frequency, which can be set to a frequency less than a Nyquist frequency determined given based on a sampling rate.

The filtered analog signal can be converted to a digital signal at block 625. A digital filter can be applied to the digital signal at block 630. Digital filter can reduce DC signal components. Digital filtering can be performed using a linear or non-linear filter. Filters can include, e.g., a finite or infinite impulse response filter or a window function (e.g., a Hanning, Hamming, Blackman or rectangular function). Filter characteristics can be defined to reduce DC signal contributions while preserving high-frequency signal components.

The filtered signal can be analyzed at block 635. As described in further detail herein, the analysis can include micro-analyses, such as categorizing individual segments of the signal (e.g., into sleep stages, arousal or non-arousal and/or intended movements). The analysis can alternatively or additionally include macro-analyses, such as characterizing an overall sleep quality or muscle activity.

As noted above, in some instances, multiple devices cooperate to perform process 600. For example, a multi-electrode device 400 of FIG. 4 can perform blocks 605-625, and a remote device (e.g., a server, computer, smart phone or interface device 405) can perform blocks 630-635. It will be appreciated that to facilitate such shared process operation, devices can communicate to share appropriate information. For example, after block 625, a multi-electrode device 400 can transmit the digital signal (e.g., using a short-range network or WiFi network) to another electronic device, such as interface device 500 of FIG. 5. The other electronic device can receive the signal and then perform blocks 630-635.

Though not explicitly shown in process 600, raw and/or processed data can be stored. The data can be stored on a multi-electrode device, a remote device and/or in the cloud. In some instances, both the raw data and a processed version thereof (e.g., identifying classifications associated with portions of the data) can be stored.

It will further be appreciated that process 600 can be an ongoing process. For example, active and reference signals can be continuously or periodically collected over an extended time period (e.g., overnight). Part or all of process 600 can be performed in real-time as signals are collected and/or data can be fully or partly processed in batches. For example, during a recording session, blocks 605-625 can be performed in real-time, and the digital signals can then be performed. Blocks 630-635 can be performed periodically (e.g., every hour or upon reaching a threshold of unanalyzed data) or at an end of the recording session.

Figure 7:
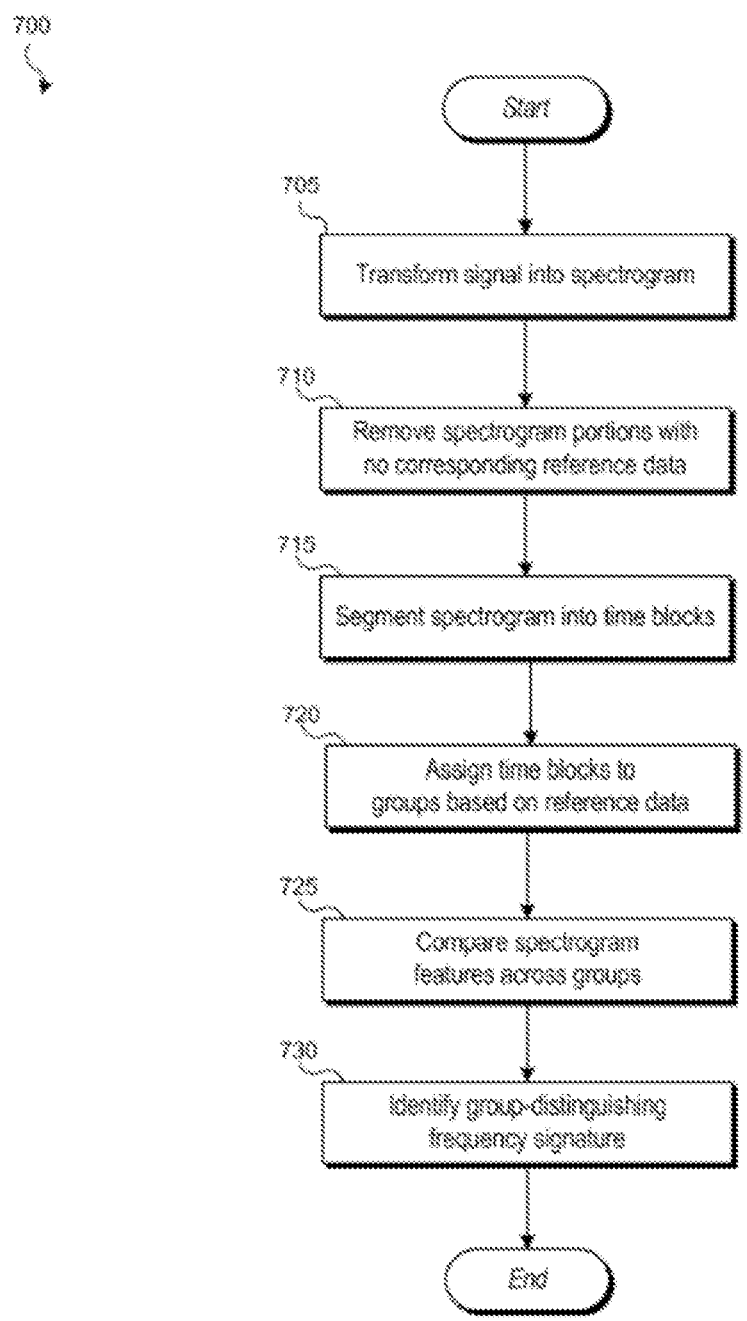
FIG. 7 is a flow diagram of a process for analyzing channel biological data to identify frequency signatures of various biological stages according to an embodiment of the present invention.

FIG. 7 is a flow diagram of a process 700 for analyzing channel biological data to identify frequency signatures of various biological stages according to an embodiment of the present invention. Part of all of process 700 can be implemented in a multi-electrode device (e.g., multi-electrode device 400 of FIG. 4) and/or in an electronic device remote from a multi-electrode device (e.g., interface device 500 of FIG. 5).

At block 705, a signal can be transformed into a spectrogram. The signal can include a signal based on recordings from electrodes positioned on a person, such as a differentially amplified and filtered signal. The spectrogram can be generated by parsing a signal into time bins, and computing, for each time bin, a spectrum (e.g., using a Fourier transformation). Thus, the spectrogram can include a multi-dimensional power matrix, with the dimensions corresponding to time and frequency.

Select portions of the spectrogram can, optionally, be removed at block 710. These portions can include those associated with particular time bins, for which it can be determined that a signal quality is poor and/or for which there is no or inadequate reference data. For example, to develop a translation or mapping from signals to physiological events, signatures of various physiological events can be determined using reference data (e.g., corresponding to a human evaluation of the data). Data portions for which no reference data is available can thus be ignored while determining the signatures.

At block 715, the spectrogram can be segmented into a set of time blocks or epochs. Each time block can be of a same duration (e.g., 30 seconds) and can (in some instances) include multiple (e.g., and a fixed number) of time increments, where time increments correspond to each recording time. In some instances, a time block is defined as a single time increment in the spectrogram. In some instances, a time block is defined as multiple time increments. A duration of the time blocks can be determined based on, e.g., a timescale of a physiological event of interest; a temporal precision or duration of corresponding reference data; and/or a desired precision, accuracy and/or speed of signal classification.

Each time bin in each time block can be assigned to a group based on reference data at block 720. For example, human scoring of EEG data can identify a sleep (or awake) stage for each time block. Time bins in a given time block can then be associated with the corresponding identified stage. As another example, the same reference data can be used to detect an arousal, which can be defined as occurring for any time bin associated with a sleep stage closer to "awake" relative to a previous time bin's stage. Time bins in a time block can then be assigned to an "arousal" group (if an arousal occurred during the block) or a "non-arousal" group. As yet another example, for a given EMG recording, a patient can indicate (e.g., verbally, using mouse clicks or using eye blinks) an intended control. To illustrate, after contracting a right jaw muscle, the patient can indicate that he intended for a cursor to move downwards. Time bins associated with the jaw contraction can then be assigned to a "downwards" group.

At block 725, spectrogram features can be compared across groups. In one instance, one or more spectrum features can first be determined for each time bin, and these set of features can be compared at block 725. For example, a strong frequency or fragmentation value can be determined, as described in greater detail herein. As another example, power (or normalized power) at each of one or more frequencies for individual time bins can be compared. In another instance, a collective spectrum can be determined based on spectrums associated with time bins assigned to a given group, and a feature can then be determined based on the collective spectrum. For example, a collective spectrum can include an average or median spectrum, and a feature can include a strong frequency, fragmentation value, or power (at one or more frequencies). As another example, a collective spectrum can include—for each time bin—a feature can include an n1% power (a power where n1% of powers at that frequency are below that power) and an n2% power (a power where n2% of powers at that frequency are below that power).

Using the features, one or more group-distinguishing frequency signatures can be identified at block 730. A frequency signature can include an identification of a variable to identify or determine based on a given spectrum to use for a group assignment. The variable can then be used, e.g., in a clustering algorithm or a data model or compared to an absolute or relative threshold in order to determine which to which state a time-bin associated with the spectrum is to be assigned. For example, a group-distinguishing frequency signature can include a particular frequency, such that a power at that frequency is to be used for group assignment. As another example, a group-distinguishing frequency can include a weight associated with each of one or more frequencies, such that a weighted sum of the frequencies' powers is to be used for group assignment.

A frequency signature can include a subset of frequencies and/or a weight for one or more frequencies. For example, an overlap between power distributions for two or more groups can be determined, and a group-distinguishing frequency can be identified as a frequency with a below-threshold overlap or as frequency with a relatively small (or a smallest) overlap. In one instance, a model can be used to determine which frequencies' (or frequency's) features can be reliably used to distinguish between the groups. In one instance, a group-distinguishing signature can be identified as a frequency associated with an information value (e.g., based on an entropy differential) above an absolute or relative (e.g., relative to other frequencies' values) values.

In one instance, block 730 can include assigning a weight to each of two or more frequencies. Then, in order to subsequently determine which group a spectrum is to be assigned to, a variable can be calculated that is a weighted sum of (normalized or unnormalized) powers. For example, block 725 can include using a component analysis (e.g., principal component analysis or independent component analysis), and block 730 can include identifying one or more components.

Figure 8:
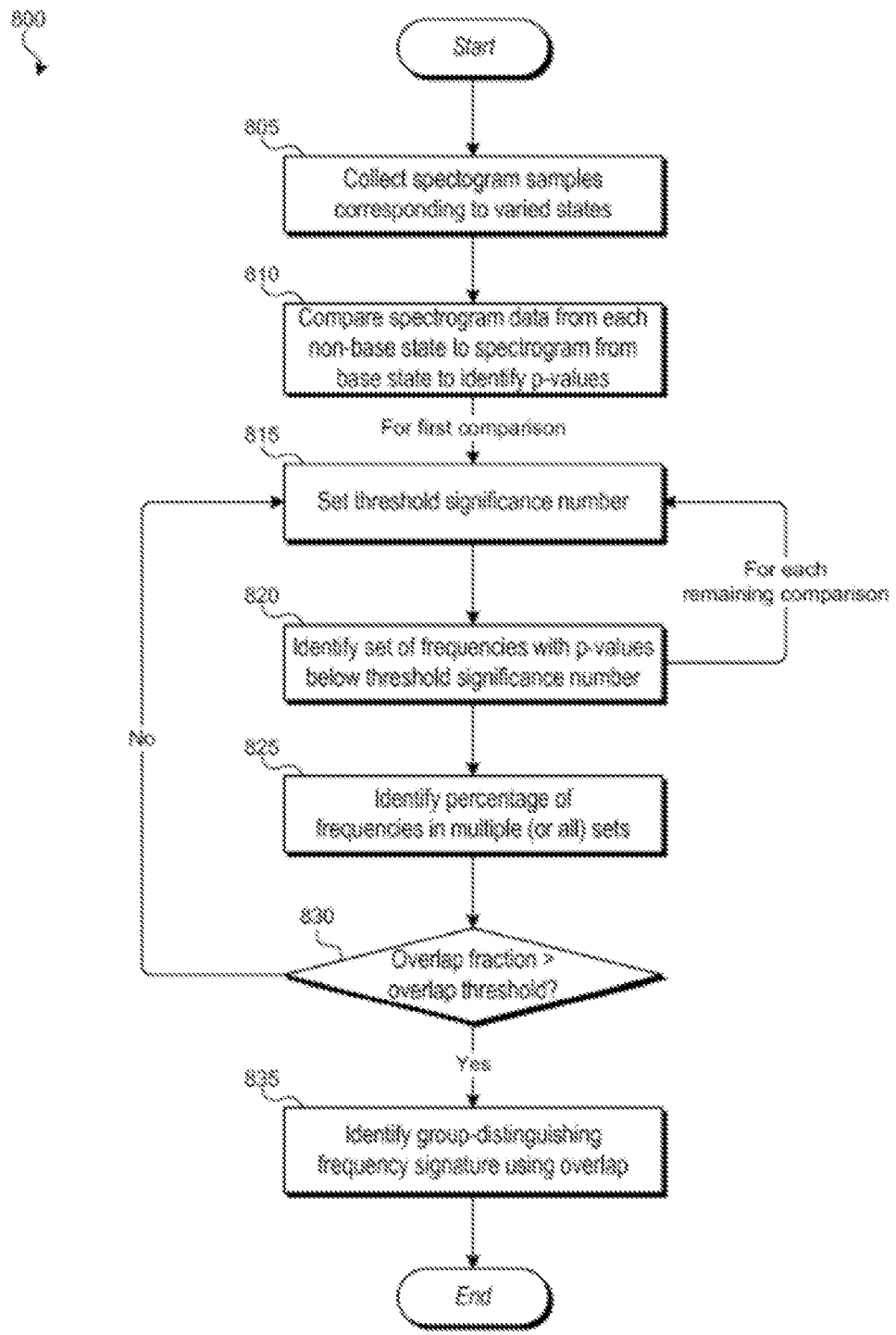
FIG. 8 is a flow diagram of a process for analyzing channel biological data to identify frequency signatures of various biological stages according to an embodiment of the present invention.

FIG. 8 is a flow diagram of a process 800 for analyzing channel biological data to identify frequency signatures of various biological stages according to an embodiment of the present invention. Part of all of process 800 can be implemented in a multi-electrode device (e.g., multi-electrode device 400 of FIG. 4) and/or in an electronic device remote from a multi-electrode device (e.g., interface device 500 of FIG. 5).

At block 805, spectrogram samples corresponding to various physiological states can be collected. In some instances, at least some states correspond to sleep stages or sleep periods with particular attributes. For example, samples can be collected both from a sleep period and an awake period, such that the samples an include data from one or more stages of sleep and an awake stage. As another example, using human sleep-stage scoring, samples can be collected to ensure (e.g., equal or roughly equal) representation of an awake stage and from each sleep stage. As another example, samples can be collected from a sleep period that includes (e.g., based on a patient's report or human scoring) frequent arousals and from a sleep period that includes infrequent arousals. In some instances, the collected samples are based on recordings from a single individual. In another, they are based on recordings from multiple individuals.

In some instances, at least some states correspond to intention states. For example, samples (e.g., based on EMG data) can be collected such that some data corresponds to an intention to induce a particular action (e.g., move a cursor upwards or downwards) and other data corresponds to no such.

The spectrogram data can include a spectrogram of raw data, a spectrogram of filtered data, a once-normalized spectrogram (e.g., normalizing a power at each frequency based on powers across time bins for the same frequency or based on powers across frequencies for the same time bin), or a spectrogram normalized multiple times (e.g., normalizing a power at each frequency at least once based on normalized or unnormalized powers across time bins for the same frequency and at least once based on normalized or unnormalized powers across frequencies for the same time bin).

At block 810, spectrogram data from a base state (e.g., an alert stage, a low-arousal sleep state, or an intention not to move a cursor) can be compared to spectrogram data from each of one or more non-bases state (e.g., a sleep stage, a frequent-arousal sleep state or an intention to move a move a cursor in a particular direction) to identify a significance value. In one instance, for a comparison between the base state and a single non-base state, a frequency-specific significance value can include a p-value and can be determined for each frequency based on a statistical test of the distributions of powers in the two states.

Blocks 815-820 are then performed for each pairwise comparison between a non-base state (e.g., sleep stage) and a base state (e.g., awake). A threshold significance number can be set at block 815. The threshold can be determined based on a distribution of the set of frequency-specific significance values and a defined percentage (n%). For example, the threshold significance number can be defined as a value at which n% (e.g., 60%) of the frequency-specific significance values are below the threshold significance number.

A set of frequencies with frequency-specific significance values below the threshold can be identified at block 820. Thus, these frequencies can include those that (based on the threshold significance number) sufficiently distinguish the base state from the non-base state.

Blocks 815 and 820 are then repeated for each additional comparison between the base state and another non-base state. A result then includes a set of an n%-most significant frequencies associated with each non-base state.

At block 825, frequencies present in all sets (or a threshold number of sets) are identified. Thus, the identified overlapping frequencies can include those amongst the n%-most significant frequencies in distinguishing each of multiple non-base states from a base state.

A determination can be made, at block 830, as to whether the overlap percentage is greater than an overlap threshold. When it is not, process 800 can return to block 815, where a new (e.g., higher) threshold significance number can be set. For example, a threshold percentage (n %) used to define the threshold significance number can be incremented (e.g., by 1%), so as to include more frequencies in the set identified at block 820.

When the overlap is determined to be greater than the overlap threshold, process 800 can continue to block 835, where one or more group-distinguishing frequency signatures can be defined using frequencies in an overlap between the sets. The signature can include an identification of a subset of frequencies in the spectrogram and/or a weight for each of one or more frequencies. The weight can be based on, e.g., a frequency's frequency—specific significance values for each of one or more base-state versus non-base-state comparisons or (in instances where the overlap assessment does not require that the identified frequencies be present in all sets of frequencies) a number of sets that include a given frequency. In some instances, the signature includes one or more components defined by assigning weights frequencies in the overlap. For example, a component analysis can be performed using state assignments and powers at frequencies in the overlap to identify one or more components.

Figure 9:
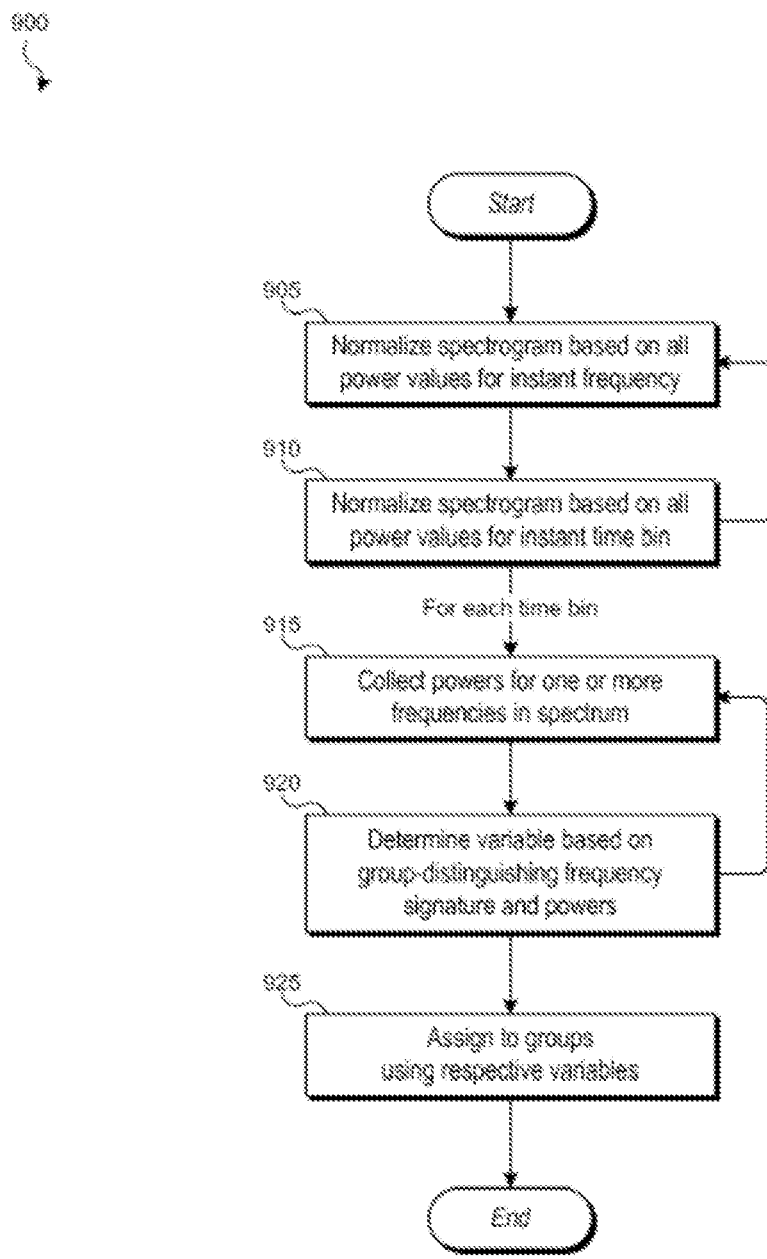
FIG. 9 is a flow diagram of a process for normalizing a spectrogram and using a group-distinguishing frequency signature to classify biological data according to an embodiment of the present invention.

Subsequent analyses (e.g., of different data) can be focused on the group-distinguishing frequency signature(s). In some instances, a spectrogram (e.g., normalized or unnormalized spectrogram) can be cropped to exclude frequencies not defined as being a group-defining frequency. For example, process 800 can be initially performed to identify group-defining frequencies, and process 700 (e.g., subsequently analyzing different data) can crop a signal's spectrogram using the group-defining frequencies before comparing FIG. 9 is a flow diagram of a process 900 for normalizing a spectrogram and using a group-distinguishing frequency signature to classify biological data according to an embodiment of the present invention. Part of all of process 900 can be implemented in a multi-electrode device (e.g., multi-electrode device 400 of FIG. 4) and/or in an electronic device remote from a multi-electrode device (e.g., interface device 500 of FIG. 5).

At blocks 905 and 910, a spectrogram built from recorded biological electrical signals (e.g., EEG or EMG data) is normalized (e.g., once, multiple times or iteratively). In some embodiments, the spectrogram is built from channel data for one or more channels, each generated based on signals recorded using a device that fixes multiple electrodes relative to each other or that tethers multiple electrodes to each other.

A first normalization, performed at block 905, can be performed by first determining—for each frequency in the spectrogram—a z-score of the powers associated with that frequency (i.e., across all time bins). The powers at that frequency can then be normalized using this z-score value.

A (optional) second normalization, performed at block 910, can be performed by first determining—for each time bin in the spectrogram—a z-score based on the powers associated with that time bin (i.e., across all time bins). The powers at that time bin can then be normalized using this z-score value.

These normalizations can be repeatedly performed (in an alternating manner) a set number of times or until a normalization factor (or a change in a normalization factor) is below a threshold. In some instances, only one normalization is performed, such that either block 905 or block 910 is omitted from process 900. In some instances, the spectrogram is not normalized.

For each time bin in the spectrogram, the corresponding spectrum can be collected at block 915. At block 920, one or more variables can be determined for the time bin based on the spectrum and one or more group-distinguishing frequency signatures. For example, a variable can include a power at a select frequency identified in a signature. As another example, a variable can include a value of a component (e.g., determined by calculating a weighted sum of power values in the spectrum) that is defined in a signature. Thus, in some instances, block 920 includes projecting a spectrum onto a new basis. Blocks 915 and 920 can be performed for each time bin.

At block 925, group assignments are made based on the associated variable. In some instances, individual time bins are assigned. In some instances, collections of time bins (e.g., individual epochs) are assigned to groups. Assignment can be performed, e.g., by comparing the variable to a threshold (e.g., such that it is assigned to one group if the variable is below a threshold and another otherwise) or by using a clustering or modeling technique (e.g., a Gaussian Naïve Bayes classifier). In some instances, the assignment is constrained such that a given feature (e.g., time bin or time epoch) cannot be assigned to more than a specified number of groups. This number may, or may not (depending on the embodiment), be the same as a number of groups or states (both base and non-base states) used to determine one or more group-distinguishing frequency signatures. The assignments can be generic (e.g., such that a clustering analysis produces an assignment to one of five groups, without tying any group to a particular physiological significance) or state specific.

Further, at each time point, a fragmentation value can be defined. The fragmentation value can include a temporal fragmentation value or a spectral fragmentation value. For the temporal fragmentation value, a temporal gradient of the spectrogram can be determined and divided into segments. The spectrogram can include a raw spectrogram and/or a spectrogram having been normalized 1, 2 or more times across time bins and/or across frequencies (e.g., a spectrogram first normalized across time bins and then across frequencies). A given segment can include a set of time bins, each of which can be associated with a vector (spanning a set of frequencies) of partial-derivative power values. For each frequency, a gradient frequency-specific variable can be defined based on the partial-derivative power values defined for any time bin in the time block and for the frequency. For example, the variable can be defined as a mean of the absolute values of the partial-derivative power values for the frequency. A fragmentation value can be defined as a frequency with a high or highest frequency-specific variable. A spectral fragmentation value can be similarly defined but can be based on a spectral gradient of the spectrogram. High fragmentation values can be indicative of a sleep-stage disturbance.

Figure 10:
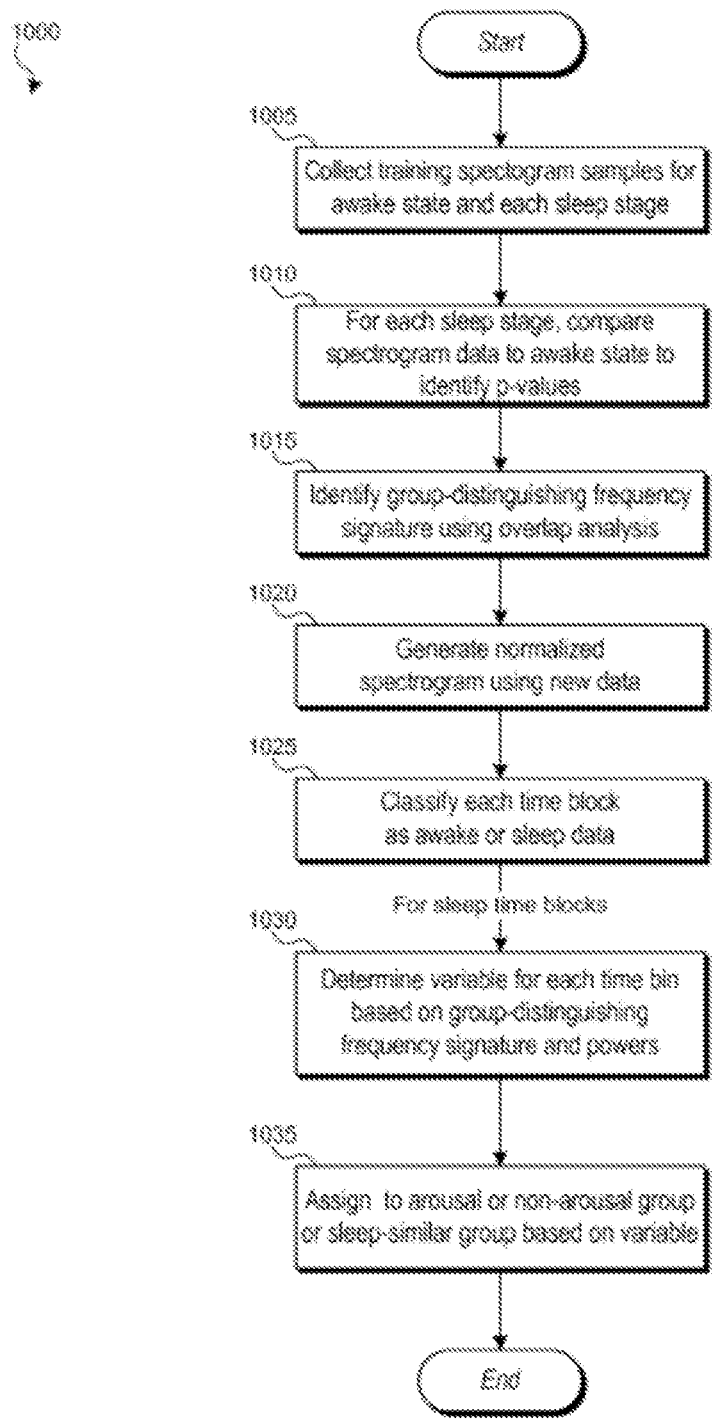
FIG. 10 is a flow diagram of a process for analyzing channel biological data to identify arousals according to an embodiment of the present invention.

FIG. 10 is a flow diagram of a process 1000 for analyzing channel biological data to identify arousals according to an embodiment of the present invention. Part of all of process 1000 can be implemented in a multi-electrode device (e.g., multi-electrode device 400 of FIG. 4) and/or in an electronic device remote from a multi-electrode device (e.g., interface device 500 of FIG. 5).

Blocks 1005 and blocks 1010 of process 1000 can, respectively, correspond to blocks 805 and 810 of process 800 in FIG. 8. In process 1000, however, the base state is defined as an awake state, and each of multiple sleep stages (e.g., stages 1-3 and REM) is defined as a non-base state.

At block 1015, a group-distinguishing frequency signature can be identified using an overlap analysis, such as an analysis as described with respect to blocks 815-835 of process 800 shown in FIG. 8. The signature can include, for example, a projection into a new basis.

At block 1020, new EEG data can be received from a device described herein or another recording device. A spectrogram can be constructed as described herein and normalized. The normalization can include one or more normalizations, as described (for example) with reference to blocks 905 and 910 of process 900.

The spectrogram can be divided into time blocks (e.g., 30-second time blocks), and each block can be classified as "awake" or "sleep" at block 1025. This designation can be performed using any of a variety of techniques, which can include analyzing variables for the block corresponding to the determined signature, analyzing powers at particular frequencies or frequency bands or analyzing which frequencies have pronounced normalized powers.

One or more time blocks classified in the sleep category can be further analyzed to detect any arousals occurring within the block. Thus, at block 1030, a variable can be determined for each time bin based on the group-distinguishing frequency signature identified at block 1015 and on powers in a spectrum for the time bin.

The variable can be used to either assign the bin or collection of bins (e.g., a time epoch) to an arousal group or a non-arousal group at block 1035. In some instances, the assignment as made by determining whether the particular variable more closely aligns with similar variables based on awake data as compared to variables based on stable sleep data. Thus, even brief arousals can be detected.

The following examples are provided to further illustrate the embodiments of the present invention, but are not intended to limit the scope of the invention. While they are typical of those that might be used, other procedures, methodologies, or techniques known to those skilled in the art may alternatively be used.

AROUSAL-DETECTION EXAMPLES

FIGS. 11-14 illustrate examples of automated arousal detections performed using process 1000. For each figure, a single-channel EEG recording of one night of sleep was analyzed, and analysis of a portion of the data is shown. The top plot shows automated detection of arousals as detected using process 1000 (each detection being indicated by a top vertical bar) and manual detection of arousals (each detection indicated by a bottom vertical bar). The bottom plot shows a hypnogram, which identifies a manual assessment as to whether the signal corresponded to an awake state or to sleep stage (and which sleep stage of sleep). A sleep/awake state was assigned (as shown in the bottom hypnograms) for each 30-second period. The arousal detection occurred on a finer time scale. Thus, arousals could be detected even during periods corresponding to a flat hypnogram. For each data set, sensitivity, specificity and accuracy variables were calculated by comparing the automated and manual arousal detections.

Example 1

General Arousal Detection

Figure 11:
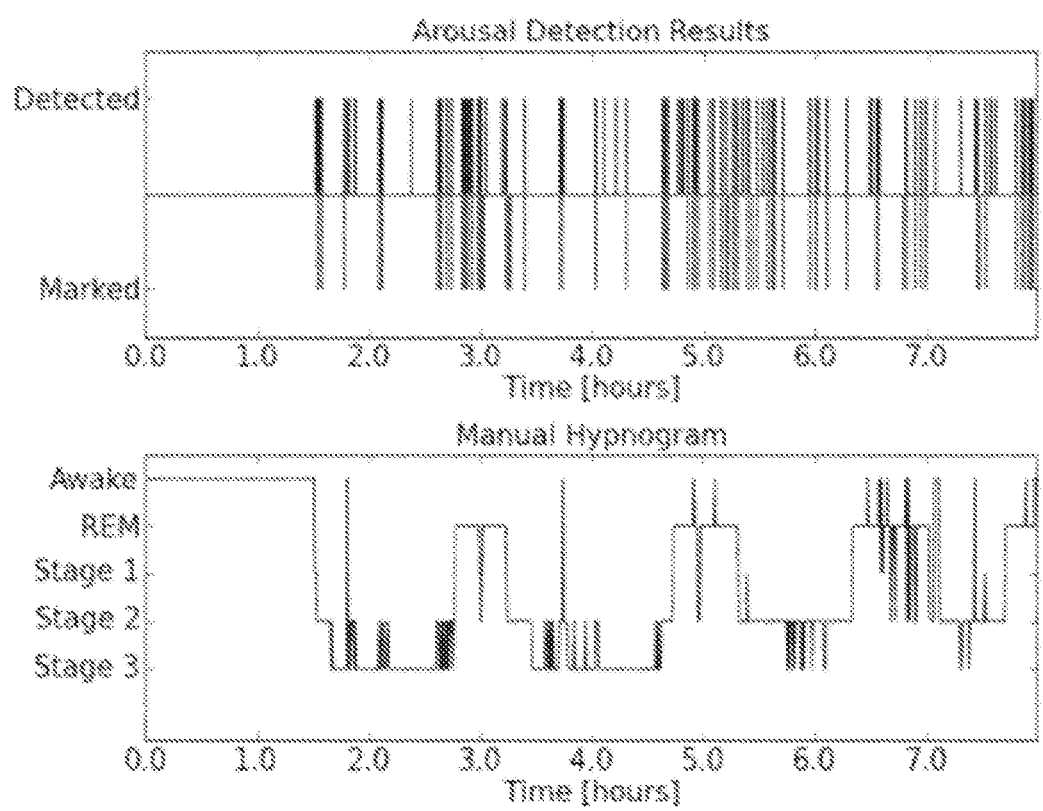
FIGS. 11-14 illustrate examples of automated arousal detections.

As shown in FIG. 11, the manual and automated detections largely track each other. The automated detection's sensitivity was 72.7%, its specificity was 99.0% and its accuracy was 98.4%. This automated arousal detection can further be combined with manual or automated sleep-stage detection to determine a percentage of the stage's sleep interrupted by arousals. In this situation (using the manual sleep-stage detection) and/or an amount of sleep time between arousals. For this data set, the average sleep time between arousals was only 2.4 minutes, and the maximum was only 19 minutes. Thus, the arousal detection can be used to quickly analyze sleep data and to provide quantifiable indications pertaining to a sleep quality.

Example 2

Arousal-Based Treatment Analysis

Figure 12A:
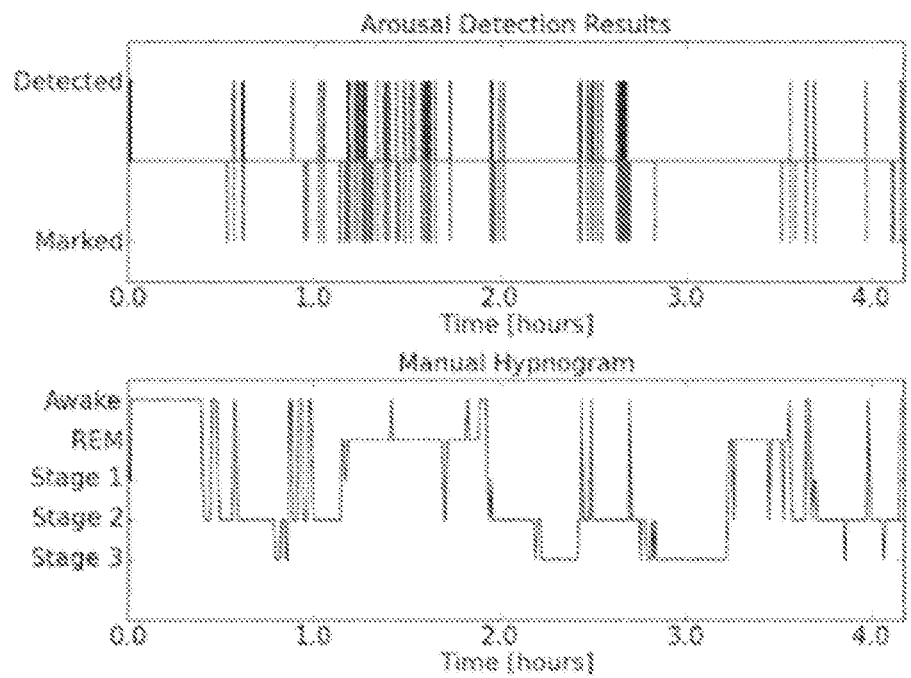
Figure 12B:
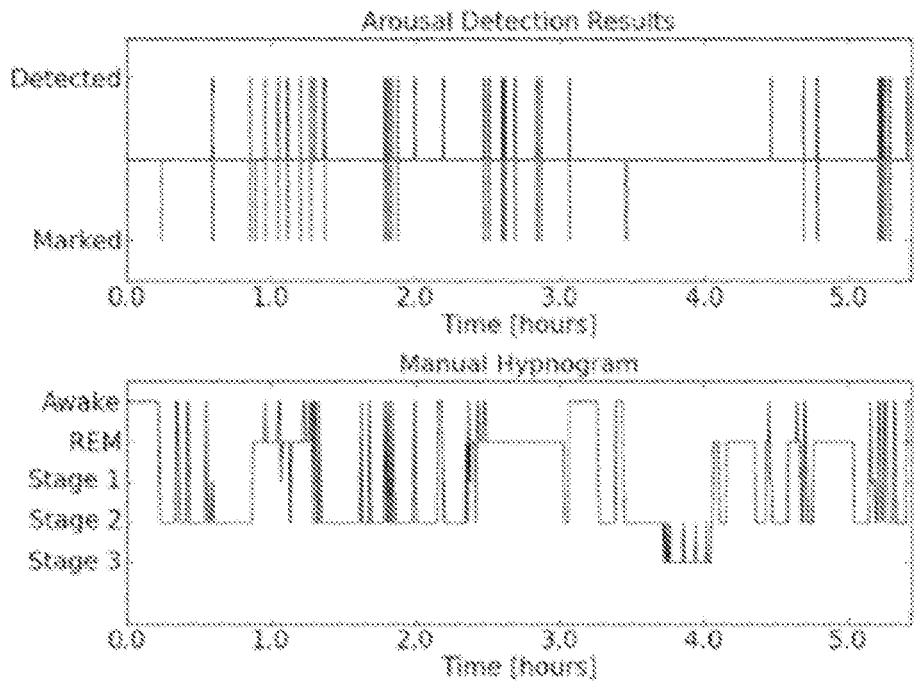

Arousal detection can further provide an assessment of a treatment. FIGS. 12A and 12B show analyses of sleep data for a first patient without a continuous positive airway pressure (CPAP) (FIG. 12A) treatment and then with the CPAP treatment (FIG. 12B). Again, the automated arousal detections track the manual detections. Further, differences corresponding to the CPAP presence are pronounced using both types of detections. Overall, arousals were present in 2.1% of the time bins for the without—CPAP data set (4.0% in stage-1 sleep, 3.0% in stage-2 sleep, 0% in stage 3 sleep and 2.3% in REM) and only 1.2% of the time bins for the CPAP data set (2.9%) in stage-1 sleep, 1.2% in stage-2 sleep, 0% in stage-3 sleep and 1.4% in REM). Thus, arousals decreased by 43% in the CPAP data set suggesting that the treatment was effectively.

Figure 13A:
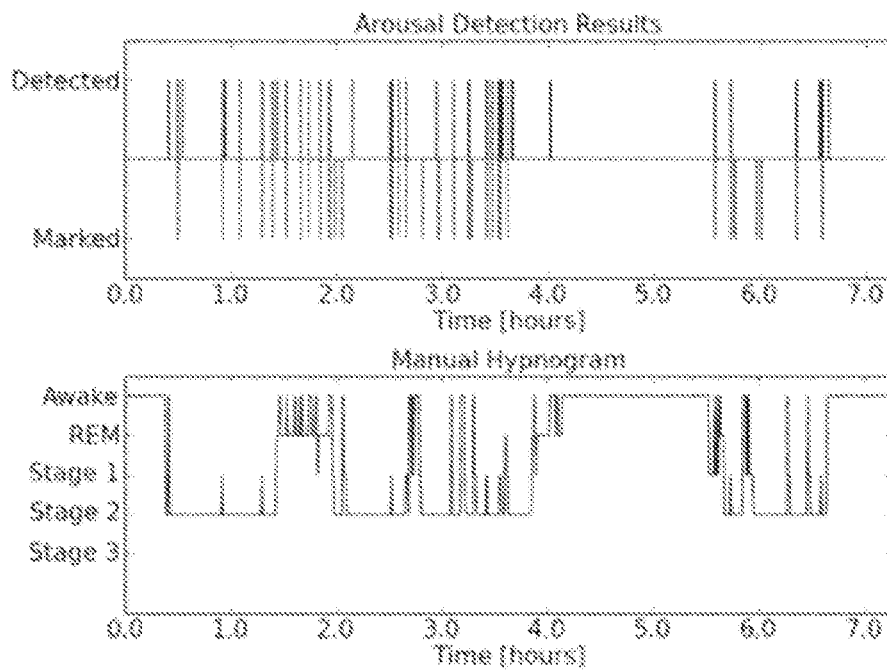
Figure 13B:
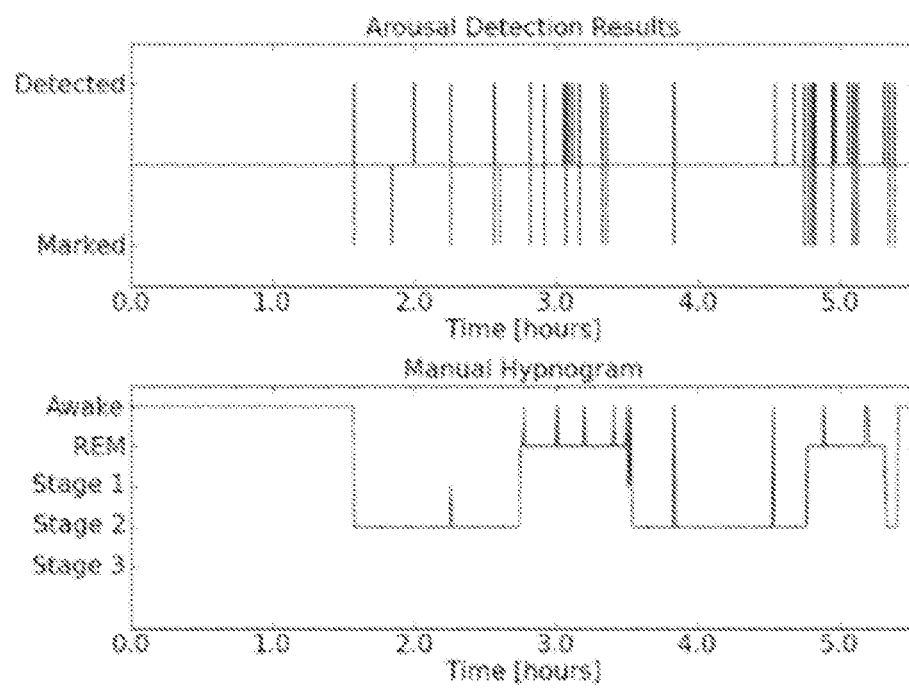

FIGS. 13A and 13B show analyses of similar data but for a second patient. Overall, arousals were present in 1.1% of the time bins for the without—CPAP data set (2.0% in stage-1 sleep, 0.9%) in stage-2 sleep, 0% in stage 3 sleep and 1.2% in REM) and only 0.9% of the time bins for the CPAP data set (2.5% in stage-1 sleep, 0.6% in stage-2 sleep, 0% in stage-3 sleep and 1.3% in REM). Interestingly, for this patient, arousals are thus decreasing by 18% overall, though arousals in REM are increasing by 8%.

Example 3

Arousal-Based Analysis of Drug Effect

Arousal-based statistics were used to compare four cohorts in a drug study. One of the cohorts includes a placebo cohort. The other three correspond to a drug, each cohort being associated with a different dose of the drug. For each patient, a mean time between arousals was determined. An ANOVA was performed to determine whether the average inter-arousal time significantly differed for any cohort. The second cohort was associated with p-values of 0.004, 0.002 and 0.004 when compared to each of the other three cohorts was associated with short mean inter-arousal times. Thus, a drug's efficacy and/or side-effect profile can be examined using automated arousal detection.

Example 4

Detection of Excessive Arousals

Figure 14:
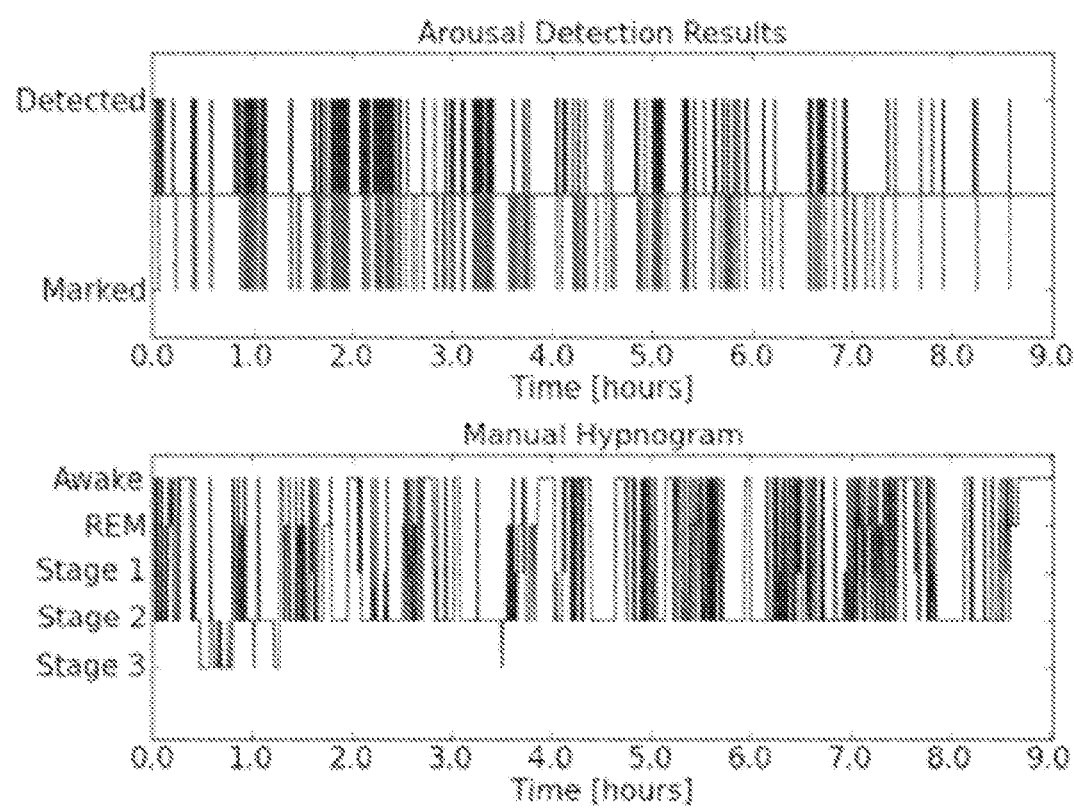

FIG. 14 shows arousal detection in a patient who experienced many arousals. The average inter-arousal time was only 1.4 minutes. Such frequent arousals can be suggestive or indicative of insomnia, and can be used for diagnosis, monitoring and/or treatment-assessment purposes.

As described herein, using group-differentiating frequency signatures can be useful to classify biological electrical signals. In one embodiment, this technique relies on utilizing power from a normalized or unnormalized spectrogram of biological data to assign each time bin to a physiologically relevant group. In some embodiments, classification can instead or additionally depend on an identification of a frequency (for a time bin) that is associated with a particular characteristic.

Figure 15:
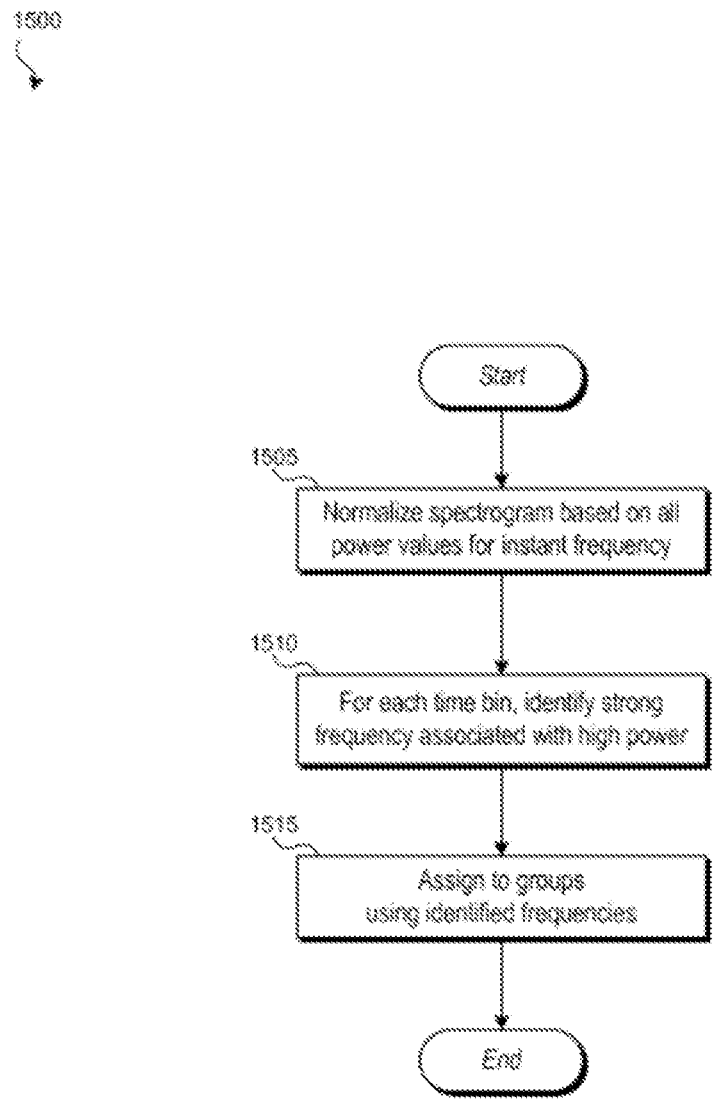
FIG. 15 is a flow diagram of a process for normalizing a spectrogram and identifying frequencies to classify biological data according to an embodiment of the present invention.

FIG. 15 is a flow diagram of a process 1500 for normalizing a spectrogram and identifying frequencies to classify biological data according to an embodiment of the present invention. Part of all of process 1500 can be implemented in a multi-electrode device (e.g., multi-electrode device 400 of FIG. 4) and/or in an electronic device remote from a multi-electrode device (e.g., interface device 500 of FIG. 5).

Blocks 1505 of process 1500 can correspond to blocks 905 of process 900. Thus, as will be appreciated from the above disclosure, each value in a spectrogram generated from biological electrical data can be normalized based on other values at a same frequency but at different time bins. In some instances, no spectral normalization is performed (though in some embodiments it is).

At block 1510, for each time bin, a frequency associated with a high or highest normalized power can be identified as a strong frequency for the time bin. The identified strong frequencies can be used to assign each time bin or each collection of time bins (e.g., time epoch) to a group at block 1515. For example, particular sleep stages can be associated with activity in particular frequency bands. Thus, e.g., strong frequencies in particular bands can bias towards assignments to particular sleep stages. The assignment can be performed, e.g., using a clustering analysis, a component analysis, a data model and/or a comparison relative to one or more thresholds.

Figure 16:
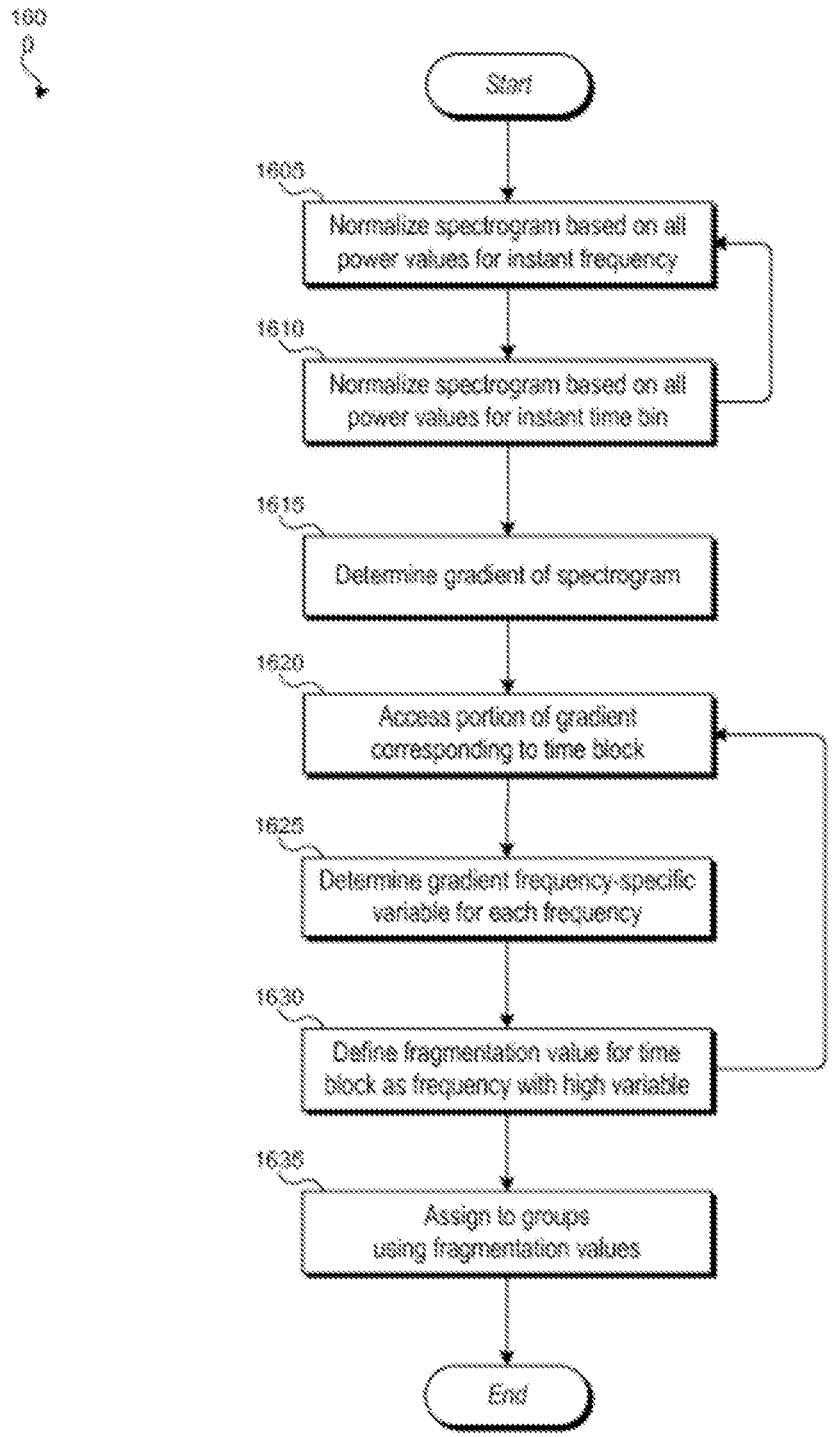
FIG. 16 is a flow diagram of a process for normalizing a spectrogram and using a gradient to identify frequencies to classify biological data according to an embodiment of the present invention.

In some embodiments, a spectrogram can be processed to emphasize temporal changes in power. Frequencies associated with large change values can then be used to classify portions of a recording. FIG. 16 is a flow diagram of a process 1600 for normalizing a spectrogram and using a gradient to identify frequencies to classify biological data according to an embodiment of the present invention. Part of all of process 1600 can be implemented in a multi-electrode device (e.g., multi-electrode device 400 of FIG. 4) and/or in an electronic device remote from a multi-electrode device (e.g., interface device 500 of FIG. 5).

Blocks 1605 and 1610 of process 1600 can correspond to blocks 905 and 910 of process 900. Thus, as will be appreciated from the above disclosure, a spectrogram generated from biological electrical data can be normalized one, two or more times based on power variations (e.g., a spread) across horizontal or vertical vectors in the spectrogram.

At block 1615, a temporal gradient can be determined based on the normalized spectrogram. It will be appreciated that block 1615 can be modified to include other processing that quantifies (for each frequency) temporal power changes. The gradient can be divided into (e.g., fixed-duration) time blocks or time epochs, and a portion of the gradient defined for a given time block can be accessed at block 1620.

At block 1625, a gradient frequency-specific variable can be determined for each frequency based on the gradient portion for the time block. For a given frequency, the variable can depend on each value in the gradient portion corresponding to the frequency. The variable can include a population statistic, such as a mean, median or maximum. In some instances, an absolute value of the gradient is calculated and used for a population analysis to determine the variable.

At block 1630, a fragmentation value can be defined—for a given time block—as a frequency for the time block that is associated with a high (or highest) gradient frequency-specific variable. Thus the fragmentation value can include a frequency associated with large power modulations in time. Process 1600 can then return to block 1620 to determine a fragmentation value for another time block.

The identified fragmentation values can be used for assignments of the time blocks at block 1635. For example, arousals can be associated with strong power variations in particular frequency bands. In some instances, in addition to or instead of analyzing the frequencies associated with high gradient values, the gradient values themselves (e.g., at the fragmentation—value frequency and/or other frequencies) can be used for the assignment. The assignment can be performed, e.g., using a clustering or component analysis or a data model.

Figure 17:
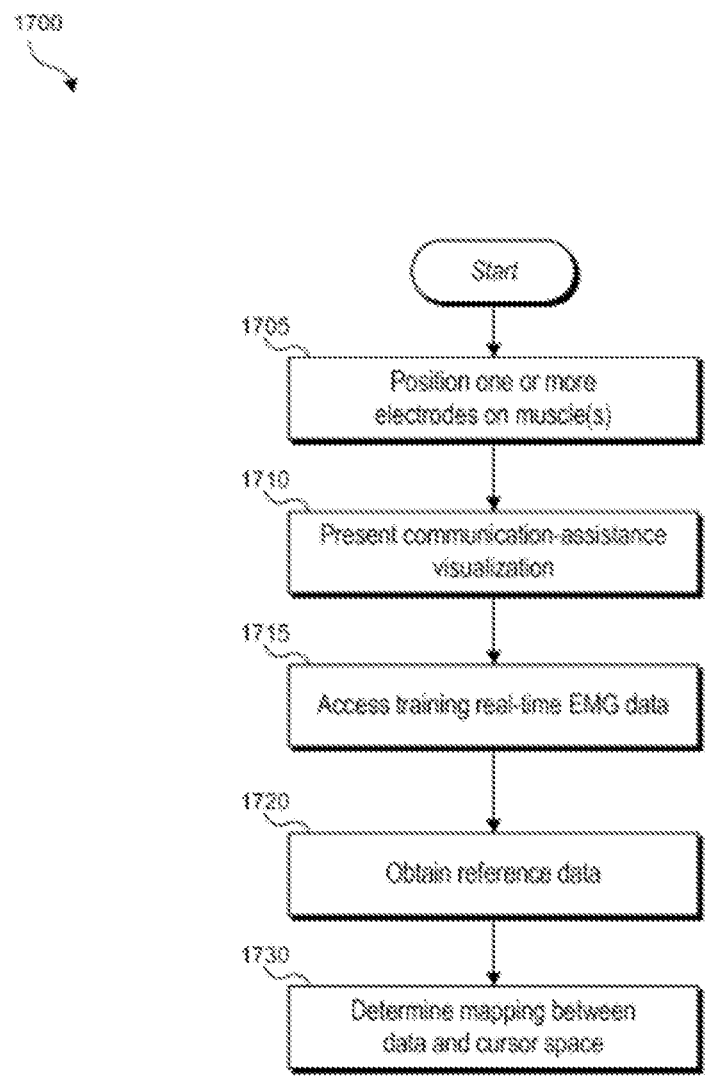
FIG. 17 is a flow diagram of a process for determining a mapping of EMG data using reference data to according to an embodiment of the present invention.

Recorded biological electrical data can, in some instances, be used to assist in a user's communication effort. FIG. 17 is a flow diagram of a process 1700 for determining a mapping of EMG data using reference data to according to an embodiment of the present invention. Part of all of process 1700 can be implemented in a multi-electrode device (e.g., multi-electrode device 400 of FIG. 4) and/or in an electronic device remote from a multi-electrode device (e.g., interface device 500 of FIG. 5).

At block 1705, one or more electrodes are positioned on one or more muscles. The electrodes can include, e.g., one or more active electrodes, one or more reference electrodes and (optionally) a ground electrode. In some instances, multiple active electrodes are used, and each is positioned over a different muscle. In some instances, a single device houses an active electrode and a reference electrode (e.g., which can be fixedly positioned within the device or flexibly tethered to the device). It will, however, be appreciated that any electrode device configured to facilitate EMG data collection by the electrode can be used.

Figure 18A:
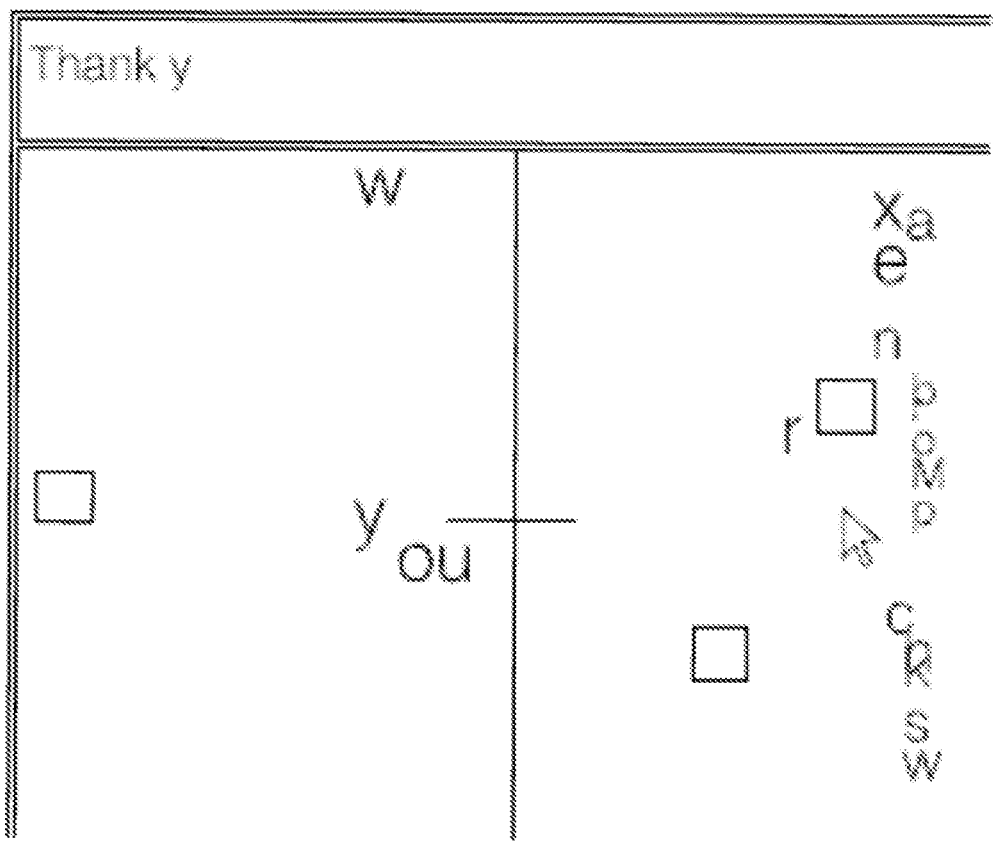
FIGS. 18A and 18B show examples of communication-assistance visualizations.
Figure 18B:
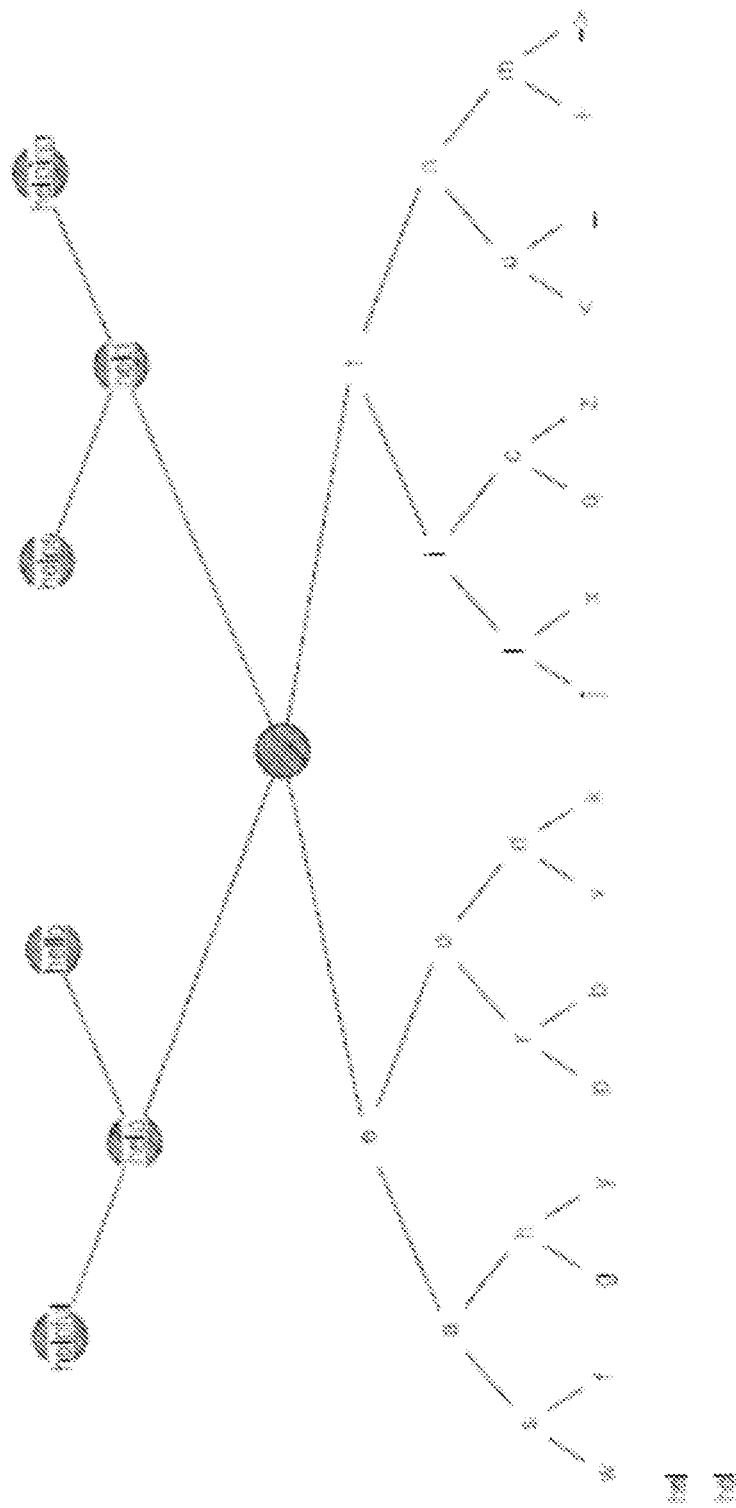

At block 1710, a communication-assistance visualization can be presented (e.g., on a screen of an interface device). FIGS. 18A and 18B show examples of communication-assistance visualizations. The visualization can include a set of letters, letter combinations, words or phrases. A cursor can be navigated to select amongst the set. A selection can continue, such that a user can gradually build a sentence or paragraph. One example of a communication-assistance visualization includes that provided by Dasher®. In some instances, no visualization is provided during a mapping-determination process.

At block 1715, real-time EMG data is accessed from the positioned electrodes. As EMG data is received from the muscles, reference data can be obtained at block 1720. The reference data can include any data indicating an intended or desired cursor movement as specified by user from whom the recordings are being collected from. For example, the reference data can include mouse movement, speech or eye blinks responsive to questions.

Using the EMG data and the reference data, a mapping can be established between the EMG data and a cursor space at block 1730. The mapping can include, e.g., a projection definition or a frequency specification (e.g., suggesting that power at a given frequency can identify a desired cursor movement). The mapping can include a group-distinguishing frequency signature, where different groups can represent different cursor movements (e.g., directions of movement). In some instances, the mapping includes a specification as to how to pre-process data. Such pre-processing can include, e.g., a normalization to perform on a spectrogram or a subtraction of data based on recordings from multiple active electrodes.

In some instances, the training performed via process 1700 can occur in anticipation of the potential that a user may soon be unable to communicate the reference data. Thus, the mapping can be established before the user's capabilities to convey intended cursor movement have diminished.

Figure 19:
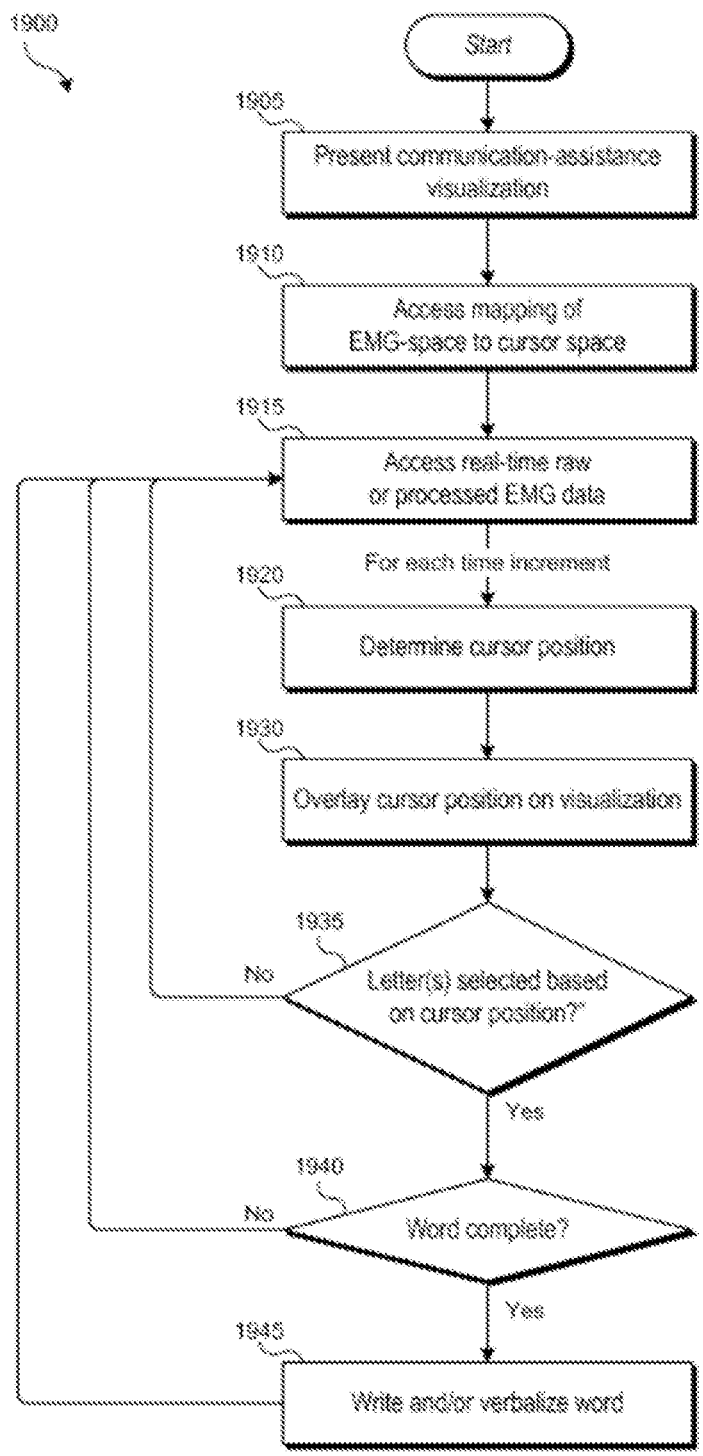
FIG. 19 is a flow diagram of a process for generating written or verbal text based on EMG data according to an embodiment of the present invention.

FIG. 19 is a flow diagram of a process 1900 for generating written or verbal text based on EMG data according to an embodiment of the present invention. Part of all of process 1900 can be implemented in a multi-electrode device (e.g., multi-electrode device 400 of FIG. 4) and/or in an electronic device remote from a multi-electrode device (e.g., interface device 500 of FIG. 5).

At block 1905, a communication assistance visualization (e.g., such as one shown in FIG. 18A or 18B) can be presented (e.g., on a display of an interface device). At block 1910, a mapping between an EMG space and a cursor space (e.g., a mapping determined at block 1730 in process 1700) can be accessed.

Real-time raw or processed EMG data can be accessed at block 1915. For example, the data can be processed such that it is transformed to form a spectrogram and/or such that it is normalized (e.g., one or more times). The data can include data received from an electrode or multi-electrode device (or a processed version thereof).

Using a time block of the data and the mapping, a cursor position can be determined at block 1920. For example, a component value corresponding to a spectrum generated using EMG data can be determined and mapped to a direction for moving the cursor.

A representation of the cursor can then be presented at the determined position on the visualization. A determination can be made at block 1935 as to whether a letter (or letter combination, word or phrase) has been selected. For example, a selection can be inferred upon the cursor having reached a representation of a letter (or letter combination, word or phrase). In one instance, another EMG signature can be used to indicate a selection.

When it is not determined that a letter has been selected, process 1900 can return to 1915, where EMG data can be monitored and processed to identify further cursor movements and to reassess letter selection. When it is determined that a selection has been made, a determination can be made at block 1940 as to whether a word is complete. This determination can be made based on what was selected at block 1935 (e.g., selecting multiple letters that would correspond to a word completion can be indicative that the work was complete), whether a next cursor movement corresponded to a space or punctuation symbol, or whether a combination of now—selected letters has formed a complete word and any formed sentence using the word is grammatically correct.

When it is not determined that the word is complete, process 1900 can return to 1915, where EMG data can be monitored and processed to identify further cursor movements and to reassess word completion. When it is determined that a word has been completed, process 1900 can continue to block 1945, where the word can be written (if not already) on a display, email or document and/or verbalized (e.g., using speakers). Thus, the collection and analysis of EMG data can aid in users' abilities to communicate even without traditional use of speech and/or hand control.

In some embodiments, techniques disclosed herein can analyze spectral characteristics of a recorded biological electrical signal. This analysis can include generating a spectrogram. Embodiments of the present invention can include normalizing the spectrogram one or more times (e.g., as described with reference to blocks 905 and 910 in process 900). Such normalization can emphasize high-frequency signal components, which can be indicative of physiological states, such as various a sleep state.

Figure 20:
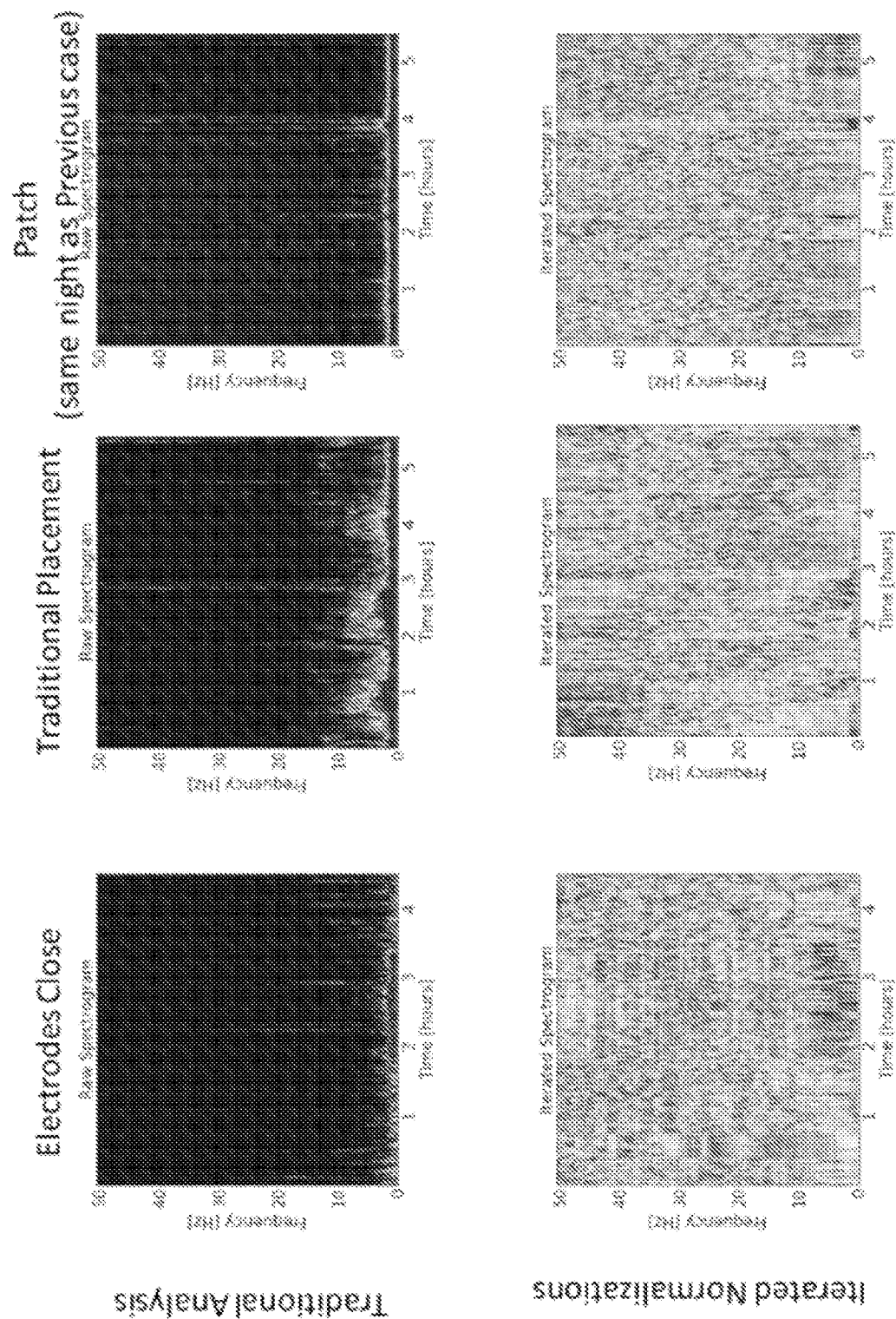
FIG. 20 shows raw spectrograms of sleep EEG data and normalized spectrograms.
Figure 21:
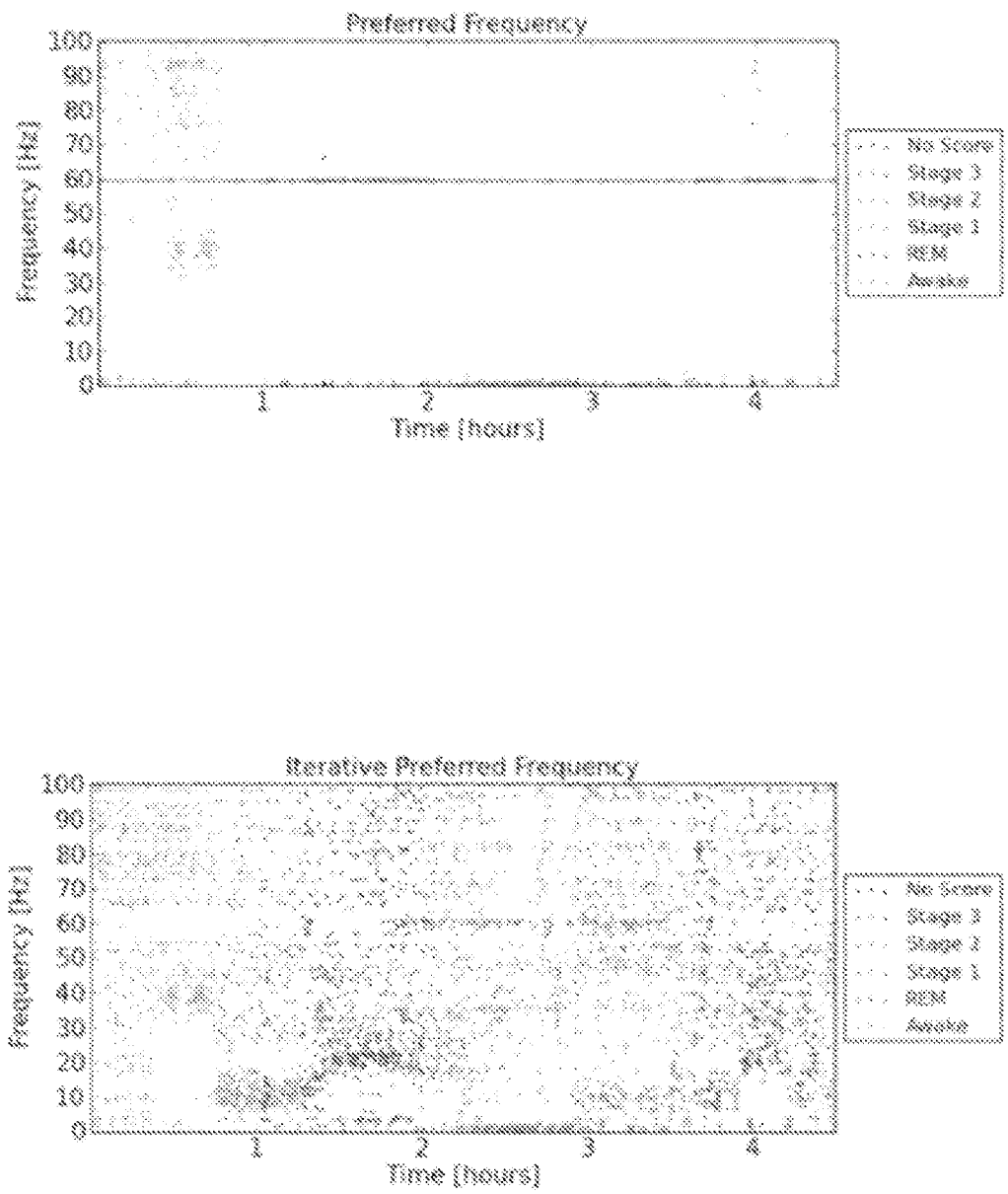
FIG. 21 shows time-series preferred-frequency graphs determined using either a raw spectrogram or normalized spectrogram.

FIGS. 20 and 21 illustrate the impact that this normalization can have on spectrogram data. In FIG. 20, the two graphs in each column are generated using the same biological signals. Meanwhile, the spectrograms in the bottom row were generated by normalizing values in the top spectrograms across time bins and across frequencies. Each column corresponds to a different recording arrangement. The left-most column used two non-fixed electrodes: an active electrode and a reference electrode and positioned them near each other for the recording. The middle column separated the two electrodes. The right electrodes included a multi-electrode device that fixedly houses the electrodes near each other.

As can be seen, the raw spectrograms are dominated by low-frequency activity and have essentially no visible activity at higher frequencies. In contract, the normalized spectrograms include prominent activity across the entire frequency range. These spectrograms also include temporally varying patterns, which suggests that activity at particular frequencies can be indicative of a sleep stage.

In FIG. 21, a time-series "preferred frequency" graph is shown determined using a raw spectrogram (top) or a spectrogram normalized across time bins and frequencies (bottom). At each time point, the preferred frequency is defined as the frequency within the spectrogram that is associated with the time point that has a highest z-score. In the top graph, the preferred frequency is typically 60Hz, is sometimes a very low frequency, and occasionally another frequency. The preferred frequencies during an awake state show more variability that for other states, though distinctions between sleep stages are difficult to discern using this variable.

Meanwhile, the preferred frequencies determined using a normalized spectrogram are much more diverse. Further, state-specific patterns are apparent, and are distinguishable even between sleep stages. Thus, FIGS. 20 and 21 illustrate that iterative normalization of spectrograms can emphasize subtle spectral state-distinguishing characteristics.

Embodiments described herein can be further extended by or detailed by disclosure in any of the following applications: U.S. application Ser. No. 13/129,185, U.S. application Ser. No. 11/431,425, U.S. application Ser. No. 13/270,099, WO/2010/057119, WO/2013/112771 and WO/2011/056679. Each of these applications is hereby incorporated by reference in its entirety for all purposes. Additionally, Low, P.S. "A new way to look at sleep: separation & convergence," eScholarship (2007), available on the World Wide Web at escholarship.org/uc/item/6250v3wk#page-56, is also hereby incorporated by reference in its entirety for all purposes.

While the invention has been described with respect to specific embodiments, one skilled in the art will recognize that numerous modifications are possible. For example, disclosures referring to signals collected by a multi-electrode device can also apply to signals collected from multiple single-electrode devices or any other one or more devices that can collect a biological electrical signal. Further, for disclosures referring to signals or channel without specifying a recording device, any device disclosed herein or any other device that can collect one or more biological electrical signals can be used. It will also be appreciated that embodiments disclosed herein can be combined in various combinations. For example, blocks from various flow charts can be combined and organized in manners not explicitly shown or described herein.

Embodiments of the present invention, e.g., in methods, apparatus, computer-readable media and the like, can be realized using any combination of dedicated components and/or programmable processors and/or other programmable devices. The various processes described herein can be implemented on the same processor or different processors in any combination. Where components are described as being configured to perform certain operations, such configuration can be accomplished, e.g., by designing electronic circuits to perform the operation, by programming programmable electronic circuits (such as microprocessors) to perform the operation, or any combination thereof. Further, while the embodiments described above may make reference to specific hardware and software components, those skilled in the art will appreciate that different combinations of hardware and/or software components may also be used and that particular operations described as being implemented in hardware might also be implemented in software or vice versa.

Computer programs incorporating various features of the present invention may be encoded and stored on various computer readable storage media; suitable media include magnetic disk or tape, optical storage media such as compact disk (CD) or DVD (digital versatile disk), flash memory, and other non-transitory media. Computer readable media encoded with the program code may be packaged with a compatible electronic device, or the program code may be provided separately from electronic devices (e.g., via Internet download or as a separately packaged computer-readable storage medium).

Although the invention has been described with reference to the above examples, it will be understood that modifications and variations are encompassed within the spirit and scope of the invention. Accordingly, the invention is limited only by the following claims.

What is claimed is:

1. A system for acquiring and processing physiological data of a subject, the system comprising:
 a) a physiological data acquisition assembly comprising a
  housing having a single cluster of electrodes, the electrodes consisting of an active electrode and a reference electrode, the active and reference electrodes being in close proximity to each other and separated by less than 3 inches within the housing, wherein the assembly has a processor and electronic circuitry having functionality to receive a reference signal collected using the reference electrode and generate a differential signal by subtracting the reference signal from the active electrode to reduce noise in an active signal collected using the active electrode; and b) a computing device, a remote server or remote network, wherein the assembly is in communication with the computing device, remote server or remote network, and wherein the physiological data acquisition assembly, the computing device, the remote server, or the remote network includes:

one or more data processors; and a non-transitory computer readable storage medium containing instructions which, when executed on the one or more data processors, cause the one or more data processors to perform a set of actions including:

generating a spectrogram using the differential signal;

normalizing the spectrogram one or more times to generate a normalized spectrogram;

determining a temporal gradient of the normalized spectrogram;

for each of multiple time bins represented in the normalized spectrogram:

identifying a segment of the normalized spectrogram that corresponds to the time bin;

determining, for the time bin, a fragmentation value based on a portion of the temporal gradient that corresponds to the time bin; and assigning the normalized spectrogram segment of the time bin to a group of a set of groups based on the fragmentation value of the normalized spectrogram segment; and generating an output based on the normalized spectrogram segments assigned to the set of groups, wherein the output: (i) characterizes a plurality of micro-arousals occurring within a sleep state; (ii) includes a movement-control signal; (iii) includes synthetic speech; or (iv) includes text presented at or transmitted by a speech-assistance interface.

2. The system of claim 1, wherein the physiological data acquisition assembly further comprises a power subsystem.

3. The system of claim 1, wherein the physiological data acquisition assembly further comprises functionality for analyzing physiological data acquired from a user.

4. The system of claim 1, wherein the physiological data acquisition assembly is configured to record, transmit or store data acquired from a user.

5. The system of claim 4, wherein the physiological data acquisition assembly further comprises functionality to encrypt acquired data.

6. The system of claim 1, wherein the physiological data acquisition assembly further comprises at least one port to charge the assembly.

7. The system of claim 1, wherein the physiological data acquisition assembly further comprises at least one port to transmit or receive data.

8. The system of claim 3, wherein the physiological data acquisition assembly further comprises a wireless communications module.

9. The system of claim 1, wherein the physiological data acquisition assembly is in communication with a remote server or a computing device.

10. The system of claim 8, wherein the physiological data acquisition assembly is in wireless communication with a remote control.

11. The system of claim 10, wherein the remote control serves as a power source or docking station.

12. The system of claim 1, wherein the physiological data acquisition assembly further comprises one or more additional sensors.

13. The system of claim 12, wherein a sensor the one or more additional sensors are selected from the group consisting of an accelerometer, GPS sensor, head positioning sensor, nasal pneumotachometer, body temperature sensor and oximeter.

14. The system of claim 12, wherein the one or more additional sensors detect a physiological parameter selected from the group consisting of body temperature, pulse, respiratory rate, respiratory volume and blood pressure.

15. The system of claim 1, wherein the differential signal is electromyography data.

16. The system of claim 1, wherein the computing device comprises a graphical display.

17. The system of claim 16, wherein generating the output comprises generating a desired text option on the graphical display.

18. The system of claim 1, wherein the computing device is selected from the group consisting of prosthetic, laptop, computer, cell phone, media player, medical device, tablet, and phablet.

19. The system of claim 1, wherein the computing device is a prosthetic, and wherein generating the output includes generating the movement-control signal, and wherein the set of actions further include transmitting the movement-control signal to the prosthetic.

20. The system of claim 1, wherein the output includes synthetic speech.

21. The system of claim 1, wherein generating the output includes:

determining one or more cursor positions on a graphical display of the computing device based on the assignment; and determining a desired text option on a graphical display of the computing device based on the one or more cursor positions.

22. The system of claim 1, wherein the output includes the movement-control signal, and wherein the set of actions further includes causing a prosthetic to move in accordance with the movement-control signal.

23. The system of claim 1, wherein generating an output based on the normalized spectrogram segments of the set of groups includes:

for a normalized spectrogram segment of the normalized spectrogram segments:

identifying a group of the set of groups assigned to the normalized spectrogram segment, wherein the group identifies a particular type of movement or a particular type of sleep;

associating, based on the identified group, the normalized spectrogram segment with the particular type of movement or the particular type of sleep; and generating the output that includes the particular type of movement or the particular type of sleep associated with the normalized spectrogram segment.

24. The system of claim 1, wherein assigning the normalized spectrogram segment of the time bin to a group of the set of groups includes performing a clustering or component analysis of the normalized spectrogram segments.

25. The system of claim 1, wherein the physiological data is electroencephalography (EEG) data.

26. The system of claim 1, wherein the physiological data is electromyography (EMG) data.

27. A method of obtaining and analyzing physiological data of a subject comprising:
  obtaining physiological data from the subject from a physiological data acquisition assembly that comprises a housing having a single cluster of electrodes, the electrodes consisting of an active electrode and a reference electrode, the active and reference electrodes being in close proximity to each other and separated by less than 3 inches within the housing, wherein the assembly has a processor and electronic circuitry having functionality to receive a reference signal collected using the reference electrode and generate a differential signal by subtracting the reference signal from the active electrode; and
  processing, using a computing system, the differential signal by performing a set of actions that includes:
  generating a spectrogram using the differential signal;
  normalizing the spectrogram one or more times to generate a normalized spectrogram;
  determining a temporal gradient of the normalized spectrogram;
  for each of multiple time bins represented in the normalized spectrogram:
    identifying a segment of the normalized spectrogram that corresponds to the time bin;
    determining, for the time bin, a fragmentation value based on a portion of the temporal gradient that corresponds to the time bin; and
    assigning the normalized spectrogram segment of the time bin to a group of a set of groups based the fragmentation value of the normalized spectrogram segment; and
  generating an output based on the normalized spectrogram segments assigned to the set of groups, wherein the output: (i) characterizes a plurality of micro-arousals occurring within a sleep state; (ii) includes a movement-control signal; (iii) includes synthetic speech; or (iv) includes text presented at or transmitted by a speech-assistance interface.

28. The method of claim 27, wherein the set of actions further comprises predicting, for each of the multiple time bins, a sleep state based on the group assignment, and wherein the output characterizes the sleep states.

29. The method of claim 27, wherein the set of actions further comprises determining an effect of a drug on the subject based on the output.

30. The method of claim 27, wherein the set of actions further comprises determining a presence or state of a disease of the subject based on the output.

31. The method of claim 30, wherein the disease is a neurological or neurodegenerative disease.

32. The method of claim 30, wherein the disease is amyotrophic lateral sclerosis (ALS) or muscular dystrophy.

33. The method of claim 27, further comprising utilizing the output to define input processed by an application operating on the computing system.

34. The method of claim 33, wherein the input includes a cursor position.

35. The method of claim 27, further comprising controlling movement of a prosthetic using the output.

36. The method of claim 27, further comprising using the output to control a cursor, text, an icon or a visual pointer displayed on a graphical user interface of a computing device.

37. The method of claim 27, further comprising generating sound via a computing device based on the output.

38. The method of claim 37, wherein the sound is audible speech.

39. The method of claim 27, wherein the physiological data is electromyography (EMG) data.

40. The method of claim 27, wherein the output characterizes arousal or alertness occurrences of the subject, thereby detecting a state of arousal or alertness of the subject.

41. The method of claim 27, further comprising characterizing a quality of sleep of the subject, wherein the output further includes a representation of the characterization of the quality of sleep.

* * * * *